(12) United States Patent
Han et al.

(10) Patent No.: US 11,419,747 B2
(45) Date of Patent: Aug. 23, 2022

(54) TERRAIN ADAPTIVE POWERED JOINT ORTHOSIS

(71) Applicant: Otto Bock Healthcare LP, Austin, TX (US)

(72) Inventors: Zhixiu Han, Acton, MA (US); Christopher Williams, Pittsburgh, PA (US); Jeff Anthony Weber, San Francisco, CA (US); Christopher Eric Barnhart, Carlisle, MA (US); Hugh M. Herr, Somerville, MA (US); Richard James Casler, Jr., Lowell, MA (US)

(73) Assignee: Otto Bock Healthcare LP, Austin, TX (US)

( * ) Notice: Subject to any disclaimer, the term of this patent is extended or adjusted under 35 U.S.C. 154(b) by 227 days.

(21) Appl. No.: 16/697,763

(22) Filed: Nov. 27, 2019

(65) Prior Publication Data
US 2020/0107951 A1    Apr. 9, 2020

Related U.S. Application Data

(62) Division of application No. 15/600,930, filed on May 22, 2017, now abandoned, which is a division of application No. 13/356,230, filed on Jan. 23, 2012, now Pat. No. 9,687,377.

(60) Provisional application No. 61/435,045, filed on Jan. 21, 2011.

(51) Int. Cl.
*A61F 5/01* (2006.01)
*A61H 3/00* (2006.01)
*A61H 1/02* (2006.01)

(52) U.S. Cl.
CPC ........... *A61F 5/0125* (2013.01); *A61H 1/024* (2013.01); *A61H 3/00* (2013.01); *A61H 2003/001* (2013.01); *A61H 2201/165* (2013.01); *A61H 2201/1642* (2013.01); *A61H 2201/5007* (2013.01); *A61H 2201/5064* (2013.01); *A61H 2201/5084* (2013.01); *A61H 2201/5097* (2013.01); *A61H 2205/10* (2013.01); *A61H 2205/102* (2013.01)

(58) Field of Classification Search
CPC .......... A61H 1/001; A61H 1/02; A61H 1/024; A61H 3/00; A61H 1/00; A61F 5/0123; A61F 5/011; A61F 5/0193; A61F 2/68; A61F 2/74

See application file for complete search history.

(56) References Cited

U.S. PATENT DOCUMENTS

2010/0179668 A1* 7/2010 Herr ...................... G01L 5/0028
623/51

* cited by examiner

*Primary Examiner* — Jason-Dennis N Stewart
(74) *Attorney, Agent, or Firm* — Goodwin Procter LLP

(57) ABSTRACT

A powered device augments a joint function of a human during a gait cycle using a powered actuator that supplies an augmentation torque, an impedance, or both to a joint. A controller estimates terrain slope and modulates the augmentation torque and the impedance according to a phase of the gait cycle and the estimated terrain slope to provide at least a biomimetic response. The controller may also modulate a joint equilibrium. Accordingly, the device is capable of normalizing or augmenting human biomechanical function, responsive to a wearer's activity, regardless of speed and terrain, and can be used, for example, as a knee orthosis, prosthesis, or exoskeleton.

31 Claims, 18 Drawing Sheets

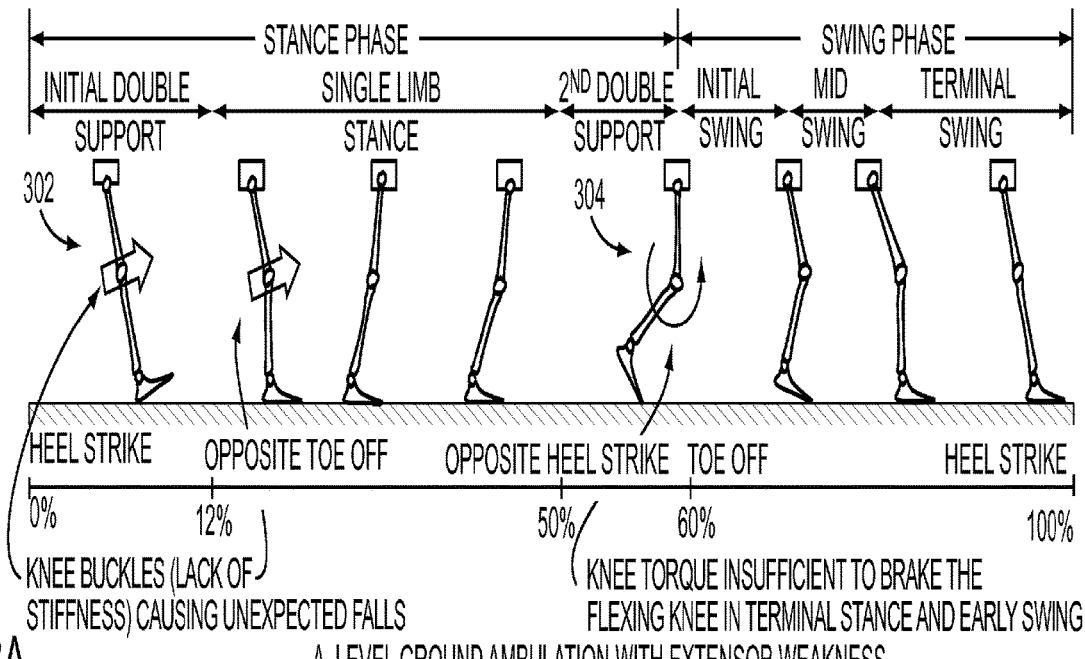
FIG.3A   A. LEVEL GROUND AMBULATION WITH EXTENSOR WEAKNESS
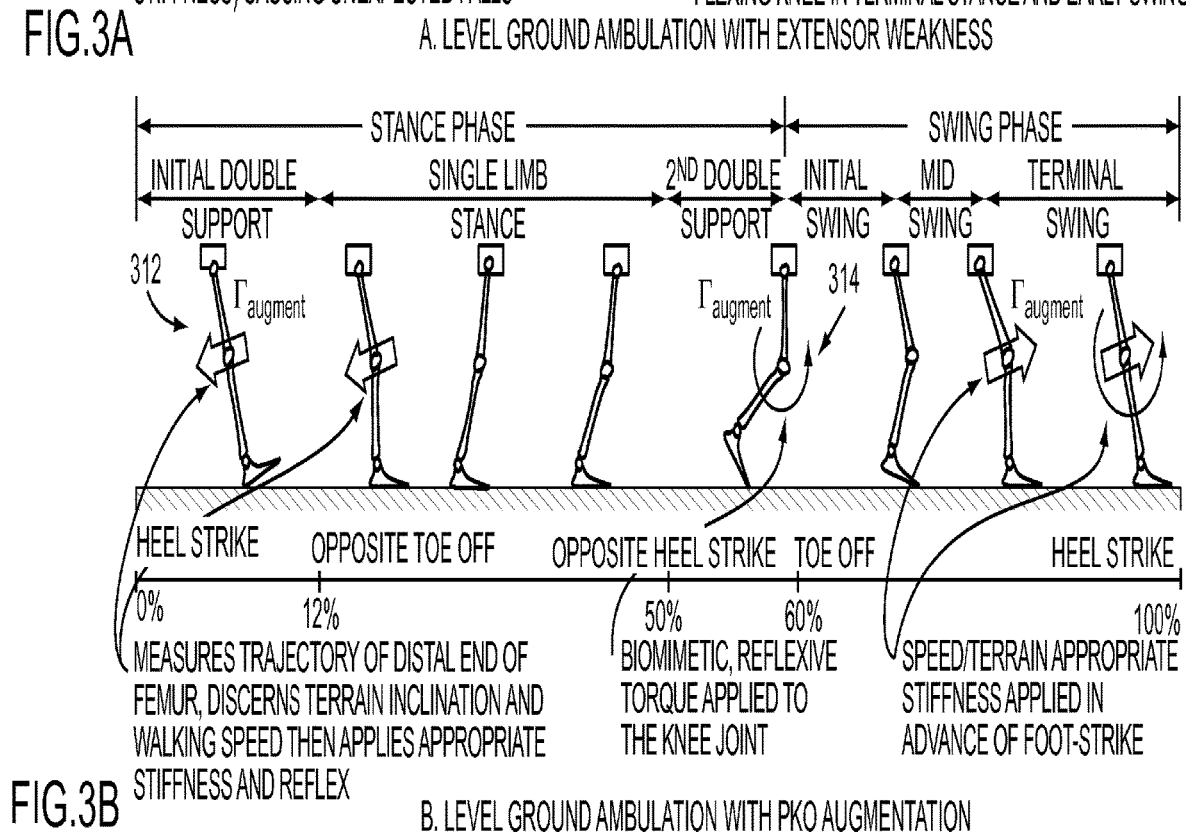
FIG.3B   B. LEVEL GROUND AMBULATION WITH PKO AUGMENTATION

| Gait Cycle Phase | Parameter | Parameter change from level-ground at self-selected walking speed ($\theta$ defined positive in flexion) | | | | | | | | |
|---|---|---|---|---|---|---|---|---|---|---|
| | | Level Ground | | | Slope/Stair Descent | | | Slope/Stair Ascent | | |
| | | $\dot{s} < \dot{s}_{ss}$ | $\dot{s} \cong \dot{s}_{ss}$ | $\dot{s} > \dot{s}_{ss}$ | $\dot{s} < \dot{s}_{ss}$ | $\dot{s} \cong \dot{s}_{ss}$ | $\dot{s} > \dot{s}_{ss}$ | $\dot{s} < \dot{s}_{ss}$ | $\dot{s} \cong \dot{s}_{ss}$ | $\dot{s} > \dot{s}_{ss}$ |
| Early Stance | $k_{es}$ | + | 0 | - | - | - | - | - | - | - |
| | $\theta_{es}$ | 0 | 0 | 0 | 0 | 0 | 0 | + | + | + |
| | $b_{es}$ | 0 | 0 | 0 | +- | + | ++ | - | - | -- |
| | $\Gamma_{es}$ | 0 | 0 | 0 | 0 | 0 | 0 | +- | + | ++ |
| Late Stance | $k_{ls}$ | 0 | 0 | 0 | 0 | 0 | 0 | 0 | 0 | 0 |
| | $\theta_{ls}$ | 0 | 0 | 0 | - | - | - | + | + | + |
| | $b_{ls}$ | 0 | 0 | 0 | + | + | + | - | - | - |
| | $P_{ff}$ | - | 0 | + | -+ | - | -- | +- | + | ++ |
| | $N$ | - | 0 | + | + | + | + | +- | + | ++ |
| Early Swing | $\theta_{brake_{esw}}$ | + | 0 | - | + | + | ++ | 0 | 0 | 0 |
| | $\Gamma_{esw}$ | $\Gamma^* \cong 0$ for ballistic trajectory to extended position | | | | | | | | |
| Late Swing | $k_{lsw}$ | 0 | 0 | + | - | - | - | - | - | - |
| | $\theta_{lsw}$ | 0 | 0 | 0 | 0 | 0 | 0 | + | + | + |
| | $b_{lsw}$ | + | 0 | - | +- | + | ++ | - | - | -- |

FIG. 4C

TERRAIN ADAPTIVE POWERED JOINT ORTHOSIS

RELATED APPLICATIONS

This application is a division of U.S. patent application Ser. No. 15/600,930, filed May 22, 2017, which is a division of U.S. patent application Ser. No. 13/356,230 filed on Jan. 23, 2012, which claims priority to and benefit of U.S. Provisional Patent Application Ser. No. 61/435,045, filed on Jan. 21, 2011, the entire content of which is hereby incorporated by reference in its entirety.

FIELD OF THE INVENTION

This invention relates generally to powered human augmentation devices, such as lower-extremity prosthetic, orthotic, or exoskeleton apparatus, designed to emulate human biomechanics and to normalize function, components thereof, and methods for controlling the same.

BACKGROUND

Approximately 65% of service members seriously injured in Iraq and Afghanistan sustain injuries to their extremities. Many of these individuals experience muscle tissue loss and/or nerve injury, resulting in the loss of limb function or substantial reduction thereof. Many devices used for the treatment of lower-extremity pathology, e.g., knee orthoses, are passive devices. Increasingly, robotic technology is employed in the treatment of individuals suffering from limb pathology, either for the advancement of therapy tools or as permanent assistive devices. Upper-extremity robotic devices provide assistance and therapy for improved reaching and manipulation and, lower-extremity robotic devices have been developed for the enhancement of locomotor function.

Although decades of research has been conducted in the area of active permanent assistive devices for the treatment of lower-extremity pathology, these devices are not designed to produce a biomimetic response, generally described in terms of joint torque, joint angle, and other related parameters as observed in a human not having substantial muscle tissue injury and not using any device to assist in ambulation. Therefore, the robotic devices usually result in unnatural ambulation and may even cause significant discomfort to the wearer.

As such, many commercially available knee orthoses remain passive and non-adaptive to the wearer even today. These devices typically stabilize the knee joint medial-laterally, and limit the extent of knee flexion and extension. As such, they do not provide power or significant assistance to the user in walking, getting out of a chair, and ascending slopes and stairs, etc.

In level-ground walking, a healthy biological knee generally behaves like a spring during early to mid-stance, where knee torque is proportional to knee angular position. Further, during slope descent, the biological knee generally behaves like a variable damper, dissipating mechanical energy as heat to lower the body's center of mass with each step. Still further, during slope ascent, the biological knee behaves like a torque source, applying a non-conservative propulsive torque throughout early to mid-stance to lift the body's center of mass upwards with each step.

Some common major complications of knee extensor weakness are an inability to apply: 1) damping control during slope/stair descent, 2) spring stiffness control during early to mid-stance in level-ground walking, and 3) non-conservative propulsive torque control for slope/stair ascent and sit-to-stand maneuvers. Due to these various complications, a patient with knee extensor weakness frequently experiences a decrease in self-selected walking speed for level-ground and slope/stair ground surfaces, as well as an increase in walking metabolism while traversing these ground surfaces. Therefore, there is a need for improved systems and methods of permanent assistive devices for the treatment of lower-extremity pathology.

SUMMARY

In various embodiments, the present invention provides devices and methods for operating/controlling such devices so as to assist humans with knee extensor weakness, normalizing and/or enhancing the wearer's self-selected walking speed and metabolic economy. This is achieved using a type of device called Powered Knee Othosis (PKO); the PKO devices are capable of capable of spring stiffness control, dissipative damping control, and non-conservative torque control in both knee flexion and extension directions, in accordance with the gait-cycle, terrain (e.g., ground slope and stairs), and walking speed. As such, the PKO devices can adaptively provide a non-conservative propulsive torque to assist the user in walking, getting out of a chair, and ascending slopes and stairs.

The PKO devices can also augment knee torque during late stance, particularly during slope and/or stair ascent. Thus, the PKO devices can provide at least a biomimetic response and optionally can be used to enhance normal biomechanical response. Offering control enhancement for both stance and swing phases, a PKO device can be used as a permanent assistive device where actuation, sensing, power, and computation are all packaged within a small, lightweight, autonomous, manufacturable, and high cycle-life package that can readily fit within a normal pant leg, and can assist humans with weak or absent quadriceps. PKO devices can also assist humans having uninjured leg musculature in activities such as carrying a heavy load over a long distance and/or increasing elevation, to enhance their strength and endurance.

In one aspect, a method for assisting a person walking on a surface with a powered human augmentation device includes a controller. The method includes using the controller for determining a phase of a gait cycle, and estimating within the gait cycle, a slope of the surface. The method also includes supplying to a joint (e.g., knee) an augmentation torque, an impedance, or both. The impedance includes a linear spring component and a damping component. The method also includes modulating the augmentation torque and the impedance based on the phase of the gait cycle and the estimated slope, to provide at least a biomimetic response.

In some embodiments, the estimated slope is indicative of a walking mode such that level-ground walking mode corresponds to a substantially zero slope, downslope walking mode corresponds to a negative slope, and upslope walking mode corresponds to a positive slope. The downslope walking mode may include descending stairs and the upslope walking mode may include ascending stairs. The joint may be a knee.

In some embodiments, the method includes estimating walking speed, and the augmentation torque and/or the impedance may be based on the estimated walking speed. If the phase of the gait cycle is determined to be one of early stance and mid stance and the estimated slope is substantially zero, the impedance may be modulated such that contribution of the linear spring component to the modulated impedance is greater than contribution of the damping component. If the phase of the gait cycle is determined to be one of early stance and mid stance and the estimated slope is negative, however, the impedance is modulated such that contribution of the damping component is increased substantially compared to contribution thereof if slope is estimated to be substantially zero. Modulating the impedance may include varying the damping component according to the negative slope.

In some embodiments, the augmentation torque includes a non-conservative propulsive torque. If the phase of the gait cycle is determined to be one of early stance and mid stance and the estimated slope is positive, the non-conservative propulsive torque is provided such that the modulated augmentation torque is greater than the modulated augmentation torque applied if the slope is estimated to be substantially zero. If the phase of the gait cycle is determined to be late stance, the augmentation torque may be modulated to correspond to a reflex torque that is related to the estimated slope.

The method may include the step of modeling a joint equilibrium as a second-order response to a joint-position goal to be achieved prior to a next phase of the gait cycle. The modeling may be performed during a swing phase of the gait cycle. The method may also include determining if the joint is substantially fully flexed, during a swing phase of the gait cycle. If the joint is determined to be substantially fully flexed, modulating includes adjusting both the augmentation torque and the impedance to be substantially zero. In some embodiments, if the phase of the gait cycle is determined to be early swing, the augmentation torque is modulated according to the joint-equilibrium model such that a joint equilibrium corresponds to the joint-position goal. The impedance may be modulated according to the joint-equilibrium model such that a joint equilibrium corresponds to the joint-position goal.

In some embodiments, estimating the slope includes kinematically reconstructing a path of the joint (e.g., a knee) within the gait cycle. The method may also include kinematically reconstructing a path of another joint (e.g., an ankle) within the gait cycle, and associating the path of the other joint with the path of the joint to estimate the slope. The kinematic reconstruction may include computing a pose and an origin of a co-ordinate frame associated with a link connected to at least one of the joint and another joint proximal to the joint. The step of computing the pose may include creating a homogeneous transformation of the co-ordinate frame. In some embodiments, the homogeneous transformation includes a 3×1 vector defining an origin of the co-ordinate frame, and a 3×3 matrix comprising unit vectors of the co-ordinate frame. At least one point within the co-ordinate frame may correspond to a link connected to the joint and/or another joint proximal to the joint. The another joint may be an ankle joint and one point within the co-ordinate frame can be a distal end and/or a proximal end of a tibia connected to the ankle.

In some embodiments, the augmentation torque is modulated according to a positive-force feedback. The augmentation torque modulated according to the positive-force feedback, in combination with a natural joint torque supplied by the human, may approximate at least a normal joint torque. The positive-force feedback may include a gain and an exponent, and modulating may include adjusting the gain or the exponent, or both, according to the estimated slope and/or walking speed. The augmentation torque may be modulated according to a scaling factor and/or may be attenuated according to a protocol. The augmentation torque may be supplied in addition to natural joint torque supplied by the person to achieve at least a pre-determined total joint torque response.

In some embodiments, modulating includes applying a closed-loop torque control at the joint. To this end, the method may include modeling the joint torque, and determining the phase of the gait cycle based on the joint torque model. The augmentation torque, the impedance, and a joint equilibrium may be modulated in order to achieve at least a target walking speed, such as a walking speed desirable to the person. The augmentation torque, the impedance, and a joint equilibrium may also be modulated in order to substantially achieve a metabolic economy in accordance with a normative reference across at least one of walking speed and terrain.

In another aspect, embodiments of the invention feature a powered human augmentation device for assisting a person walking on a surface. The device includes a powered actuator for supplying to a joint an augmentation torque and/or an impedance that includes a linear spring component and a damping component. The device also includes a controller for (i) determining a phase of a gait cycle, (ii) estimating within the gait cycle a slope of the surface, and (iii) modulating the augmentation torque and the impedance based on the phase of the gait cycle and the estimated slope to provide at least a biomimetic response.

In some embodiments, the estimated slope is indicative of a walking mode, such that level-ground walking mode corresponds to a substantially zero slope, downslope walking mode corresponds to a negative slope, and upslope walking mode corresponds to a positive slope. The downslope walking mode may include descending stairs and the upslope walking mode may include ascending stairs. The joint may be a knee.

In some embodiments, the controller is adapted to estimate walking speed, and the augmentation torque, the impedance, or both may be based on the estimated walking speed. If the controller determines the phase of the gait cycle to be one of early stance and mid stance and the estimated slope is substantially zero, the powered actuator may be adapted to provide the modulated impedance such that contribution of the linear spring component to the modulated impedance is greater than contribution of the damping component. If the controller determines the phase of the gait cycle to be one of early stance and mid stance and the estimated slope is negative, the powered actuator may be adapted to provide the modulated impedance such that contribution of the damping component is increased substantially compared to contribution thereof if slope is estimated to be substantially zero. The controller may also be adapted to modulate the damping component according to the negative slope.

In some embodiments, the augmentation torque includes a non-conservative propulsive torque and, if the controller determines the phase of the gait cycle to be one of early stance and mid stance and the estimated slope is positive, the powered actuator may be adapted to provide the non-conservative propulsive torque such that the modulated augmentation torque is greater than the modulated augmentation torque applied if the slope is estimated to be substantially zero. If the controller determines the phase of the gait cycle to be late stance, the powered actuator may be adapted to provide the modulated augmentation torque, such that the modulated augmentation torque corresponds to a reflex torque that is related to the estimated slope.

In some embodiments, the controller is adapted to model, during a swing phase of the gait cycle, a joint equilibrium as a second-order response to a joint-position goal to be achieved prior to a next phase of the gait cycle. The device may include a joint angle sensor to provide a joint angle signal to the controller. If the controller determines, based on the joint angle signal, that the joint is substantially fully flexed, the powered actuator may adapted to adjust both the augmentation torque and the impedance to be substantially zero, during a swing phase of the gait cycle. If the controller determines the phase of the gait cycle to be early swing, the augmentation torque, impedance, or both may be modulated according to the joint-equilibrium model such that a joint equilibrium corresponds to the joint-position goal.

In some embodiments, the device includes an inertial measurement unit (IMU), and the controller may be adapted to kinematically reconstruct a path of the joint within the gait cycle based on a signal from the IMU. The controller may also be adapted to estimate the slope based on the kinematic reconstruction. The IMU may include an accelerometer and/or a gyroscope. The IMU may also include a first set of sensors associated with the joint (e.g., a knee) and a second set of sensors associated with another joint (e.g., an ankle). The controller may be adapted to kinematically reconstruct a path of the other joint within the gait cycle based on signals from the second set of sensors, and to associate the path of the other joint with the path of the joint to estimate the slope of the terrain.

The augmentation torque may be modulated according to a positive-force feedback. The augmentation torque modulated according to the positive-force feedback, in combination with a natural joint torque supplied by the human, may approximate at least a normal joint torque. The positive-force feedback may include a gain and an exponent, and modulating may include adjusting the gain, the exponent, or both according to the estimated slope and/or walking speed. The controller may be adapted to modulate the augmentation torque according to a scaling factor. In some embodiments, the device includes a communication interface for receiving a protocol, and the controller may be adapted to attenuate the augmentation torque according to the received protocol. The augmentation torque may be supplied in addition to natural joint torque supplied by the person to achieve at least a pre-determined total joint torque response.

In some embodiments, the controller is adapted to apply a closed-loop torque control at the joint. The controller may be adapted to model the joint torque, and to determine the phase of the gait cycle based on the joint torque model. The powered actuator may include a series-elastic actuator, and the series-elastic actuator may include a transverse-flux motor. In some embodiments, the series-elastic actuator includes a bilateral spring and a cable drive. The series-elastic actuator may also include a buckled beam and/or a unidirectional spring.

These and other objects, along with advantages and features of the embodiments of the present invention herein disclosed, will become more apparent through reference to the following description, the accompanying drawings, and the claims. Furthermore, it is to be understood that the features of the various embodiments described herein are not mutually exclusive and can exist in various combinations and permutations. As used herein, the term "substantially" means ±10% and, in some embodiments, +5%.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which:

FIG. 3a illustrates how the knee response may become impaired when the quadriceps extensors are weakened;

FIG. 3b illustrates how the knee response of FIG. 3a can be augmented, according to one embodiment;

FIG. 4c shows adjustment of various torque and impedance parameters according to terrain and/or walking speed, according to one embodiment;

DESCRIPTION

The entire contents of each of U.S. patent application Ser. No. 12/157,727 "Powered Ankle-Foot Prosthesis" filed on Jun. 12, 2008 (Publication No. US2011/0257764 A1); U.S. patent application Ser. No. 12/552,013 "Hybrid Terrain-Adaptive Lower-Extremity Systems" filed on Sep. 1, 2009 (Publication No. US2010/0179668 A1); U.S. patent application Ser. No. 13/079,564 "Controlling Power in a Prosthesis or Orthosis Based on Predicted Walking Speed or Surrogate for Same" filed on Apr. 4, 2011; and U.S. patent application Ser. No. 13/079,571 "Controlling Torque in a Prosthesis or Orthosis Based on a Deflection of Series Elastic Element" filed on Apr. 4, 2011 are incorporated herein by reference.

Figure 1:
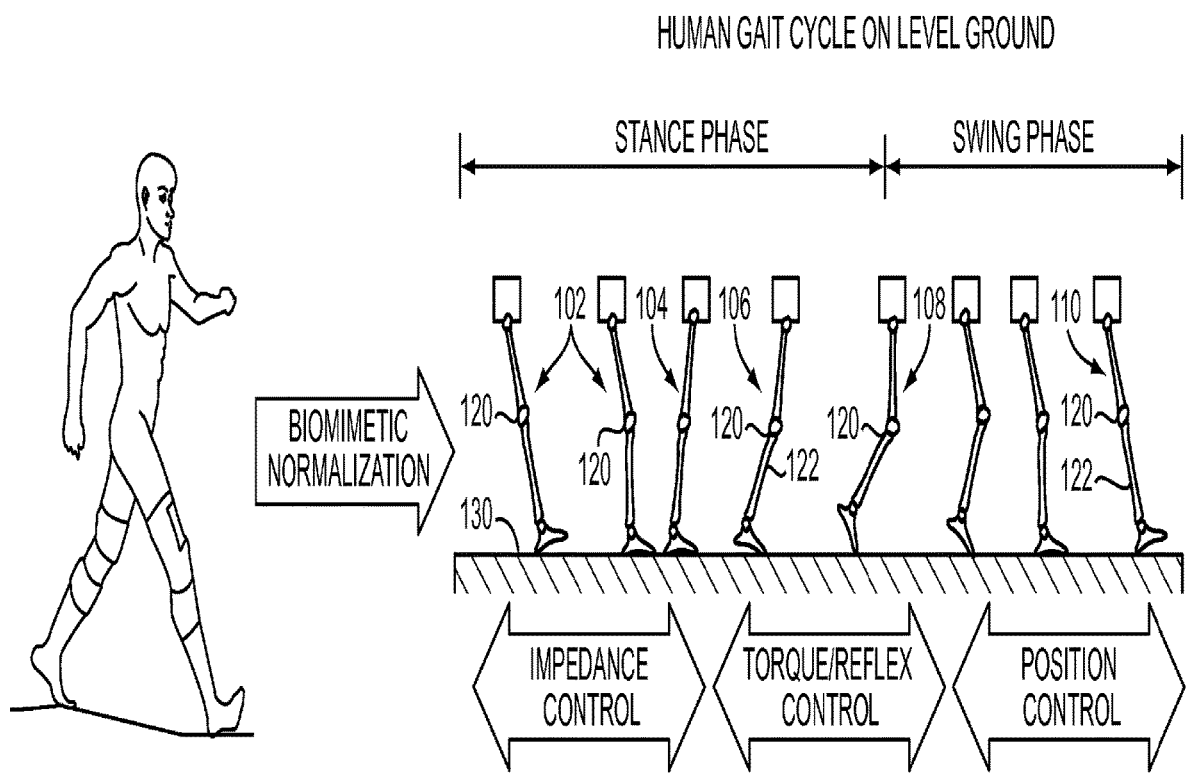
FIG. 1 illustrates biological knee function of an average human in the stance and swing phases of a human gait cycle during level-ground ambulation.

FIG. 1 illustrates biological knee function in the stance and swing phases of a human gait cycle during level-ground ambulation. Throughout early stance 102 to mid stance 104 the knee 120 typically responds as a linear spring. This form of mechanical impedance (which can take the form of a spring, inertia or damper, acting alone or in combination)

serves to cushion the foot-strike impact in accordance with the gait speed. In late-stance 106, the knee 120 generally behaves as a torque source in the form of a reflex to lift the lower leg 122 off the ground surface 130 during initiation portion 108 of the swing phase. The reflex release may arise from a positive force feedback mechanism within the gastrocnemius muscle. In the terminal portion 110 of the swing phase, the knee 120 first brakes the swinging lower leg 122 to limit heel rise after toe-off and then positions the lower leg 122 optimally for absorbing energy prior to foot strike initiation in the next gait cycle.

Figure 2:
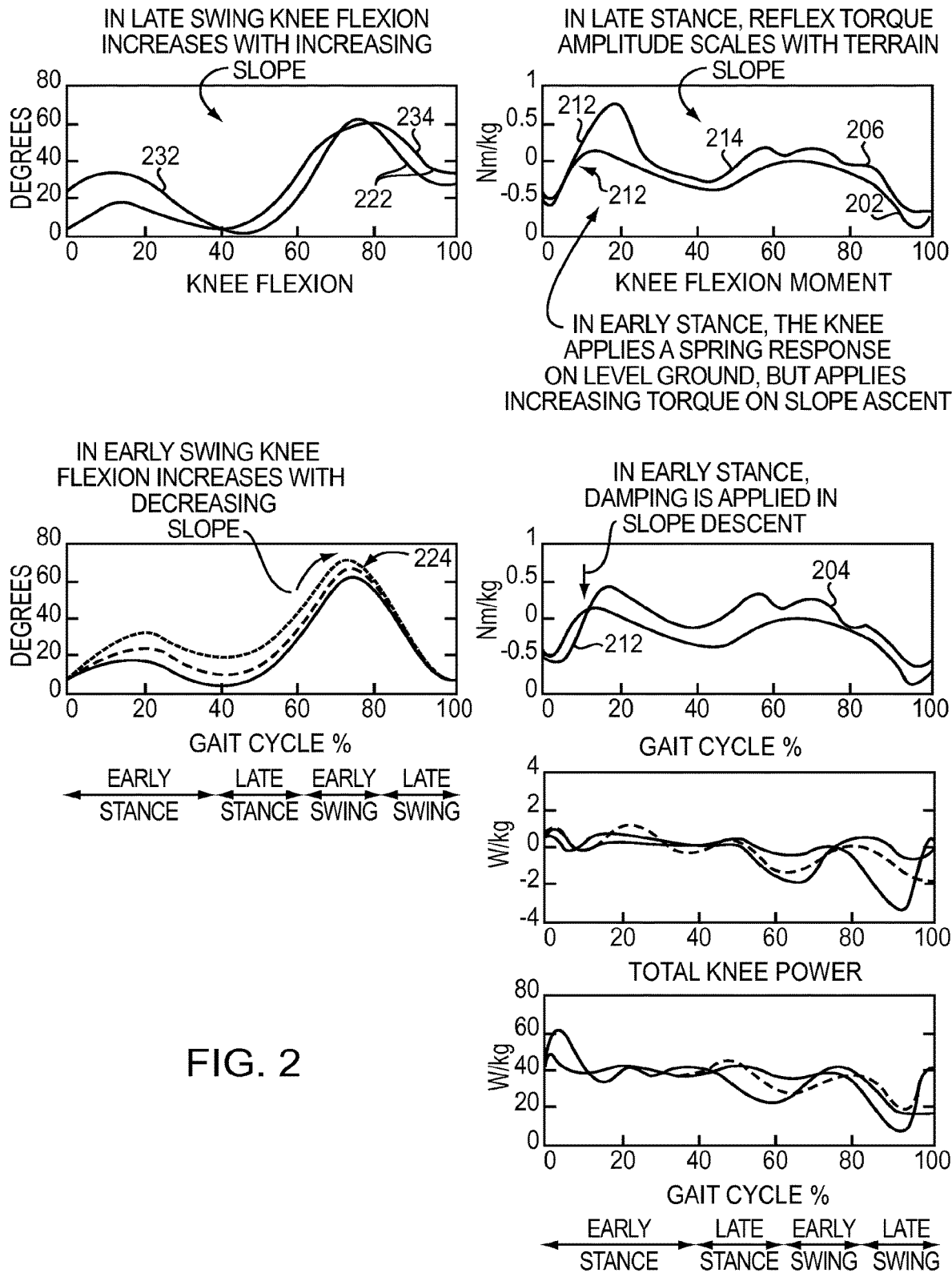
FIG. 2 illustrates how the knee response of an average human, described in terms of angle, moment (i.e., torque), and power, changes as a function of terrain slope.

Typically, the human gait adapts to terrain modality, e.g., ground slope and whether the human is ascending or descending stairs, and to walking speed so as to maintain balance and to achieve a metabolically economical movement pattern. FIG. 2 illustrates how the knee response, described in terms of angle, moment (torque), and power, changes as a function of terrain slope. For example, during level-ground walking depicted by curve 202, the biological knee behaves like a spring, where knee torque is proportional to knee angular position, during early to mid-stance 212. During slope descent, depicted by curve 204, the biological knee behaves like a variable damper, dissipating mechanical energy as heat to lower the body's center of mass with each step, during early to mid-stance 212. The variable damping generally increases as the declination angle increases. Such behavior may also be invoked during stair descent. During slope ascent, depicted by curve 206, the biological knee behaves like a torque source, applying a non-conservative propulsive torque throughout early to mid-stance 212 to lift the body's center of mass upwards with each step. Such behavior is usually also invoked upon stair ascent. A slope-dependent reflex is applied in late stance 214.

Flexion angle in the swing phase also shows terrain dependence. In slope ascent, the flexion angle just prior to foot-strike, i.e., late swing 222 of the curve 232 increases with the slope of ascent, whereas the knee flexion is invariant with the slope of descent, as depicted by the curve 234. To achieve sufficient toe clearance on descent, the knee flexion angle increases in early swing 224 as the descent becomes steeper. Though the data presented in FIG. 2 are captured at a substantially constant gait speed, it is understood that the above impedance and torque response on level ground and slopes typically changes with gait speed, in part, to account for changes in the body momentum and to deliver/absorb power accordingly.

PKO platforms 500, 800 described with reference to FIGS. 5 and 8, respectively, can discriminate terrain modality and speed within a gait cycle (intra-cycle), and can also adapt the impedance, reflex, and position response in accordance with that terrain and gait speed. Intra-cycle sensing is advantageous, because during an average walk terrain and walking speed may change frequently. The platforms 500, 800 employ a six-degree-of-freedom inertial measurement unit (IMU) capable of computing the path of the ankle joint and the distal-end of the femur (knee), from which the IMU can discriminate and discern terrain modality, including stairs and slopes, as illustrated with reference to FIG. 11b. The path of the hip can be used to augment the information from the knee and ankle. For instance, in stair ascent, the hip is generally stationary as the knee flexes, a precursor that is not evident when a wearer is traversing sloping and/or level ground.

FIG. 3a illustrates how the knee response may become impaired when the quadriceps extensors are weakened. In early stance 302, the knee stiffness can be insufficient to absorb energy either as a spring as in level-ground ambulation or as a damper in steep descent. In late stance 304, the knee torque is insufficient to "brake" the knee and to deliver sufficient reflex particularly in steep ascent and descent.

When worn by a wearer with weakened quadriceps extensors, the PKO platforms 500, 800 deliver an augmentation torque, $\Gamma_{augment}$, to normalize the response, i.e., to produce a response that may be produced by a joint (e.g., knee) of average humans not having weakened muscle tissue (e.g., quadriceps extensors) and not wearing any powered prosthetic/orthotic devices. With reference to FIG. 3b, just prior to foot-strike in early stance 312, the PKO platforms 500, 800 apply a computed knee flexion angle and set the impedance, for energy absorption, in accordance with terrain slope. The terrain slope can be inferred from the ankle and knee trajectories and with instantaneous gait speed inferred from the IMU-computed angular pitch rate of the femur and tibia.

Once the foot strikes the ground in early stance 312, the PKO platforms 500, 800 apply appropriate knee extensor torque, $\tau_{extensor}$, to achieve an impedance relation of the form:

$$\tau_{extensor} = \Gamma_0(\phi,\dot{s}) - k_{\phi,\dot{s}}(\theta - \theta_0) - b_{\phi,\dot{s}}\dot{\theta}$$

in accordance with the computed terrain slope and speed. In late stance 314, the PKO platforms 500, 800 apply additional torque and reflex in accordance with the terrain slope and the instantaneous gait speed inferred by femur and tibia pitch rates. In late stance 314, the knee extensor torque corresponds to a biologically-conceived, non-linear, positive torque feedback relation of the form:

$$\mathcal{T}_{extensor} = P_{ff\phi,\dot{s}}\left(\frac{\Gamma_{knee}}{\Gamma_0}\right)^{N_{\phi,\dot{s}}}$$

where the gain, $P_{ff_{\phi,\dot{s}}}$ is a function of terrain slope, $\phi$, and gait speed, and the exponent, $N_{\phi,\dot{s}}$, is also a function of terrain slope and gait speed. $\Gamma_{knee}$, is an intrinsic measure of knee torque in the above relation that includes the contribution of both the "locking torque" of the knee and the normalized extensor/flexor contribution. In general, both the gain and the exponent are increased to achieve the higher reflex torques needed as the slope of ascent and descent increase.

Figure 4A:
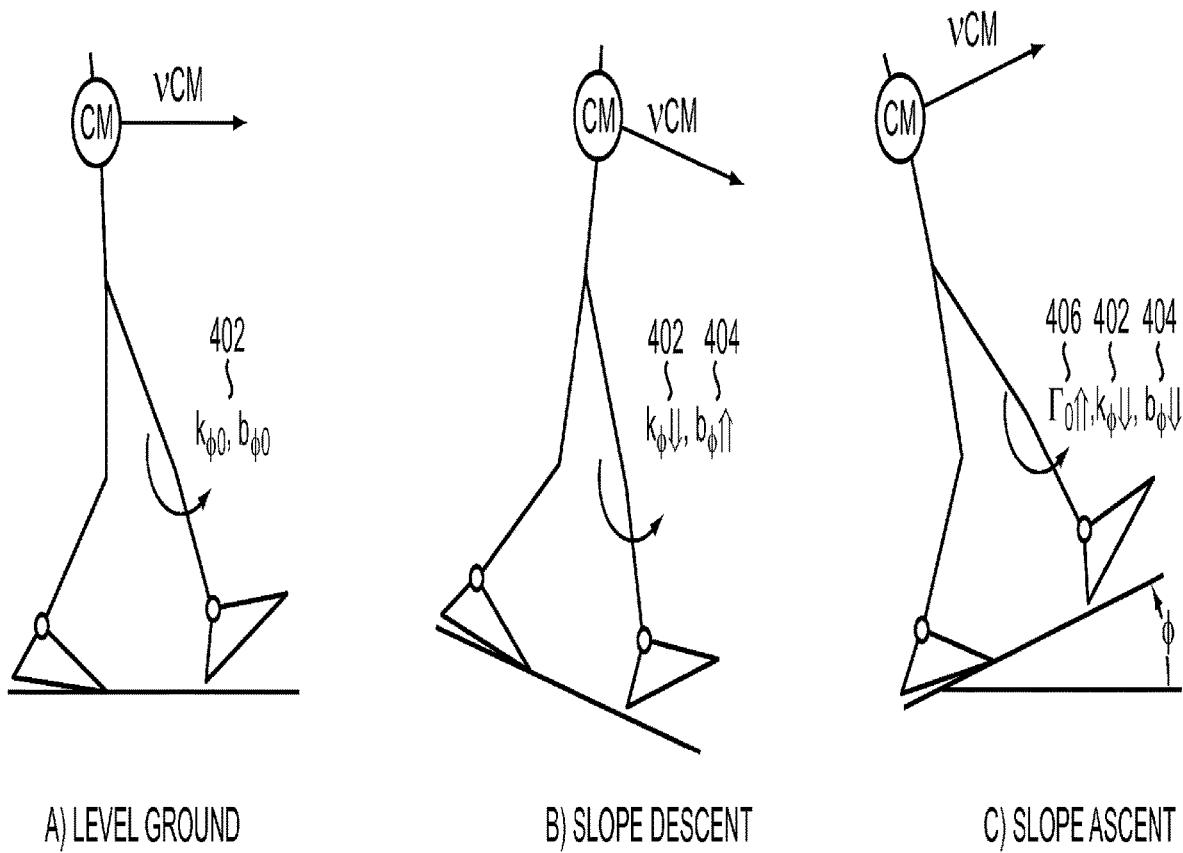
FIGS. 4a and 4b schematically illustrate, during early stance and late stance, respectively, the terrain-based modulation of various components of knee extensor torque supplied by a powered augmentation device so as to normalize the knee response, according to one embodiment.

With reference to FIG. 4a, in early stance, during level-ground walking, the linear spring component k 402 of the extensor torque applied by the PKO platforms 500, 800 is significant. While descending slope, the linear spring component k 402 is decreased and the damping component b 404 is increased, such that the damping component b 404 is significant. While ascending slope, both the linear spring k 402 and damping component b 404 are decreased and a non-conservative propulsive torque component $\Gamma_0$ 406 is increased.

Figure 4B:
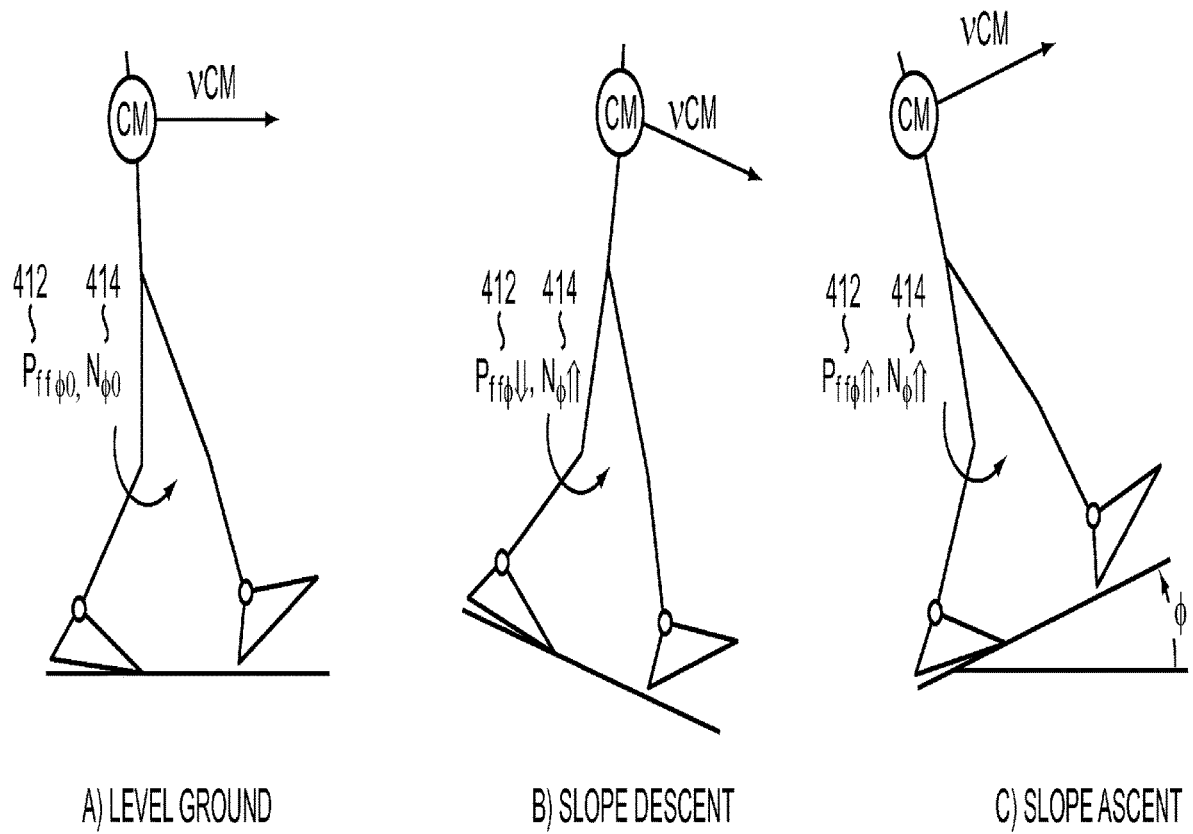

With reference to FIG. 4b, in late stance, during level-ground walking, the knee extensor torque applied by the PKO platforms 500, 800 corresponds to non-linear, positive torque feedback determined by gain 412 and exponent 414. While descending slope, the gain 412 is decreased and the exponent 414 is increased. While ascending slope, both the gain 412 and exponent 414 are increased. Adjustment of various torque and impedance parameters according to terrain and/or walking speed is described in a Table in FIG. 4c. Thus, the PKO platforms 500, 800 can emulate human knee behavior during the gait cycle by biomimetically applying impedance, torque, and joint equilibrium control in accordance with the gait cycle and speed, and augment the knee torque of the wearer to provide at least a normalized knee response.

Figure 5:
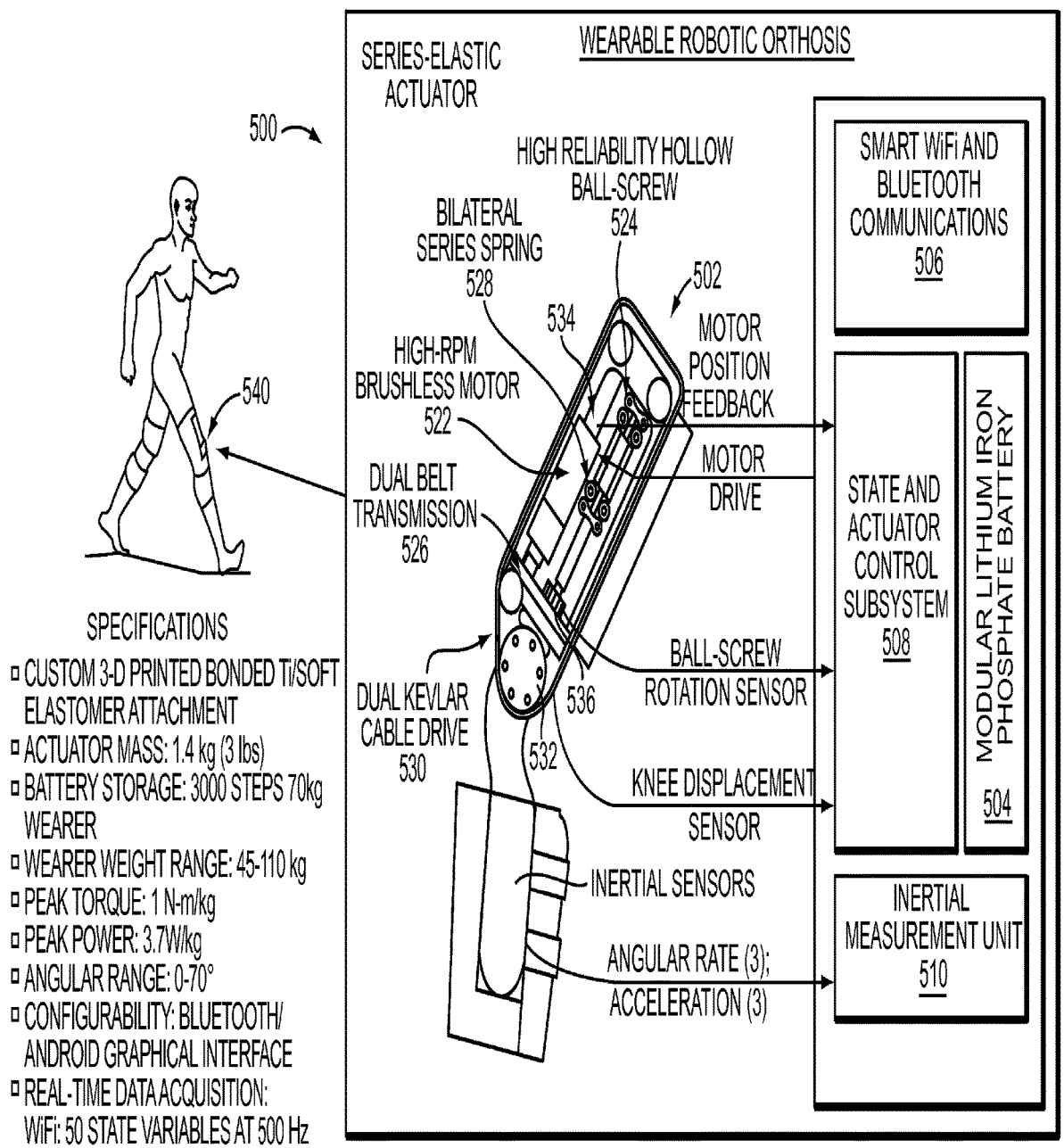
FIG. 5 schematically depicts a powered augmentation device according to one embodiment.

With reference to FIG. 5, the PKO platform 500 uses a quiet, light-weight, and rugged actuator 502. A modular battery 504 having a 3000 step capacity (typically for a wearer weighing about 70 kg with significant quadriceps extensor weakness) is used. A typical wearer may need to replace this lightweight battery pack 504 between one and two times per day. The actuator 502 can deliver at least biomimetic torque and angle response within a gait speed range from about 0 up to about 1.75 m/sec.

Optionally, the Platform 500 may employ one or two embedded wireless interfaces 506. A Bluetooth® interface may be used as the pathway for PDA-based tuning by clinicians and researchers to normalize the torque response, e.g., by specifically programming the PKO platform 500 to deliver augmentation torque $\Gamma_{augment}$ as required in each phase of the gait cycle as described below with reference to FIG. 7. A smart WiFi interface may serve as the pathway for researchers to acquire control state variables and sensory feedback from the PKO platform 500 and to synchronize this telemetry with external biomechanical instrumentation.

The actuator 502 of the PKO platform 500 can be a series-elastic actuator (SEA) to drive the powered orthosis. See, for example, U.S. Pat. No. 5,650,704 "Elastic Actuator for Precise Force Control" the disclosure of which is incorporated herein by reference. A multi-processor control system (State and Actuator Controller) 508 uses feedback from the SEA to deliver the appropriate response in accordance with the phase of the gait cycle, the terrain, and the walking speed. A three-phase brushless motor driver (Motor Driver) 522 interfaces to the State and Actuator Controller 508 to accomplish closed-loop torque control of the SEA 502. An Inertial Measurement Unit (IMU) 510, employing a three-axis rate gyro and a three-axis accelerometer, provides feedback to sense transitions between phases of the gait cycle, to measure gait speed, and to discriminate terrain modality. The WiFi/Bluetooth® communication module 506 is employed to interface directly to the State Controller and Actuator Controller 508 to facilitate data acquisition and PDA-based clinician tuning.

The SEA 502 may employ a robust ball-screw mechanism 524 driven by the high-rpm brushless motor 522 through a redundant aramid fiber twin belt transmission 526. The ball-nut 524 of the SEA 502 drives the knee 540 through a bilateral spring assembly 528 and a redundant aramid fiber cable drive 530. The bilateral spring assembly 528 can exhibit a weak stiffness in flexion and a stiffer spring in extension as would be applied in locking the knee joint. Thus in this embodiment, the bilateral spring 528 is used (i) to store energy in late stance for later release in the reflex response and (ii) to serve as a sensing means for achieving closed-loop torque control of the actuator 502. By storing energy for later release, the peak power and, hence, size and weight of the motor 522 are reduced by over 40% compared to an actuator without the spring storage, in this embodiment. Displacement of the spring 528 can be used to estimate and thereby control drive torque in a way that attenuates the effect of friction, enabling a backdrivable means of actuation that replicates biological knee operation.

A knee sensor 532, a motor-position sensor 534, and a ball-screw position sensor 536 embedded in the actuator 502 are employed to determine a state of the actuator 502 and to provide a basis for brushless motor control and for modulation of impedance, torque, and position in accordance with the phase of the gait cycle and gait speed. To this end, the State Controller and Actuator Controller 508 implements a state machine.

Figure 6:
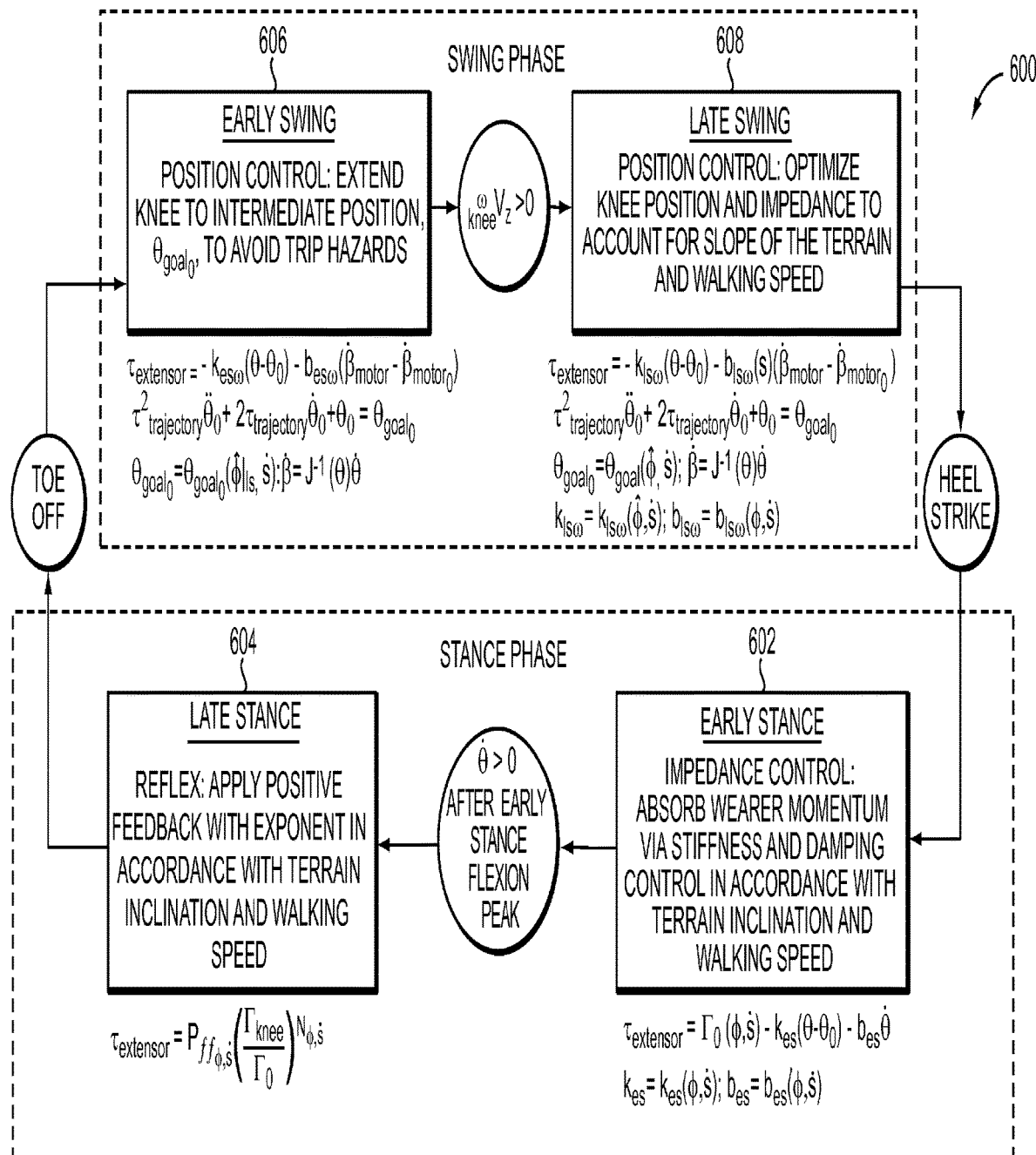
FIG. 6 illustrates the operation of a state machine of a powered augmentation device according to one embodiment.

With reference to FIG. 6, during early stance state 602, the state machine 600 adapts the PKO platform 500 to apply a linear spring and damping impedance in accordance with the gait speed and terrain angle, given by:

$$\tau_{extensor} = \Gamma_0(\phi, \dot{s}) - k_{\phi, \dot{s}}(\theta - \theta_0) - b_{\phi, \dot{s}}\dot{\theta}$$

$$k_{cp} = k_{cp}(\phi, \dot{s}); b_{cp} = b_{cp}(\phi, \dot{s})$$

Where $\tau_{extensor}$ is the commanded SEA motor torque $\theta$ is the ankle angle, $\phi$ is the terrain angle, and $\dot{s}$ is the estimated gait speed at foot-strike estimated by the IMU Transition into the early stance state 602 is accomplished by sensing by the IMU 510 the distinctive vibration that occurs when the foot strikes the ground. The impedance is configured and scaled so as to prevent buckling of the knee in accordance with walking speed and the response needed to at least normalize the augmented response of the wearer.

Transition into the late stance state 604 generally occurs when the detected knee extension angle velocity changes from negative to positive. In this state 604, a reflex response can be achieved through non-linear positive feedback as described by the relation:

$$\tau_{extensor} = P_{f\!f\phi,\dot{s}} \left(\frac{\Gamma_{knee}}{\Gamma_0}\right)^{N_{\phi,\dot{s}}}$$

In this, the reflex gain, $P_{f\!f}(\phi,\dot{s})$ and the exponent (non-linear spring), $N(\phi,\dot{s})$ are each a function of the terrain angle, $\phi$, and the estimated gait speed, $\dot{s} = \dot{s}(\dot{\Psi}_{femur}, \dot{\Psi}_{tibia})$, which is a function of the instantaneous angular rate of the tibia and femur at the time of entry in to the late stance state 604. A hard stop spring model for extreme knee extension, $\Gamma_{knee}$ ($\theta$), is used to model the wearer torque response at extremes of extension ($\theta > 0$) while the knee is locked so that at least a biomimetic response is achieved.

Transition into early swing state 606 occurs when the detected SEA 502 torque, $\Gamma_{SEA}$, approaches a programmable percentage of peak torque. In this state 606, position control is employed to brake the knee flexion velocity, to achieve proper ground clearance and heel rise during the early to mid swing phase through use of an organically-derived trajectory, $\theta_0(t)$ that smoothly decelerates to a goal position in a nearly ballistic trajectory (i.e., small torque corresponding to a lightly damped pendulum), $\theta_{goal} = \theta_{goal_0} = \theta_{goal_0}(\hat{\phi}|_{ls}, \dot{s})$:

$$\tau_{extensor} = -k_{esw}(\theta - \theta_0) - b_{esw}(\dot{\beta}_{motor} - \dot{\beta}_{motor_0})$$

$$\tau_{trajectory}{}^2\ddot{\theta}_0 + 2\tau_{trajectory}\dot{\theta}_0 + \theta_0 = \theta_{goal_0}$$

$$\theta_{goal_0} = \theta_{goal_0}(\hat{\phi}|_{ls}, \dot{s}); \dot{\beta} = J^{-1}(\theta)\dot{\theta}$$

where $\beta_{motor}$ is the motor angle corresponding to a knee angle with zero SEA spring displacement. and $\hat{\phi}|_{ls}$ is estimated terrain angle as estimated at the end of late stance using the inertial tibia and femur angular velocities.

Also in the early swing state 606, the inertial ankle and knee trajectories are computed and used to discriminate between the three modalities, i.e., slope/stair ascent, slope/stair descent, and walking on substantially level ground. This early discrimination may be used to adjust the control parameters of the State Controller and Actuator Controller 508 in advance of foot strike to achieve seamless response across the swing-stance transition.

Transition into late swing state 608 occurs when the IMU 510 detects a negative, vertical Cartesian (world-frame referenced) ankle pivot velocity, $^{W}V_{ankle\ pivot_z}$. In this state 608, position control is used with a smooth trajectory that converges to a time-varying goal point, $\theta_{goal}$, that is a function of gait speed and terrain slope, each estimated by the IMU 510 which in some embodiments uses only intra-gait-cycle information. The impedance (stiffness and damping) applied to position and velocity errors referenced to the trajectory (equilibrium), $\theta_0(t)$ may be preferably set in accordance with gait speed and terrain angle.

Figure 7:
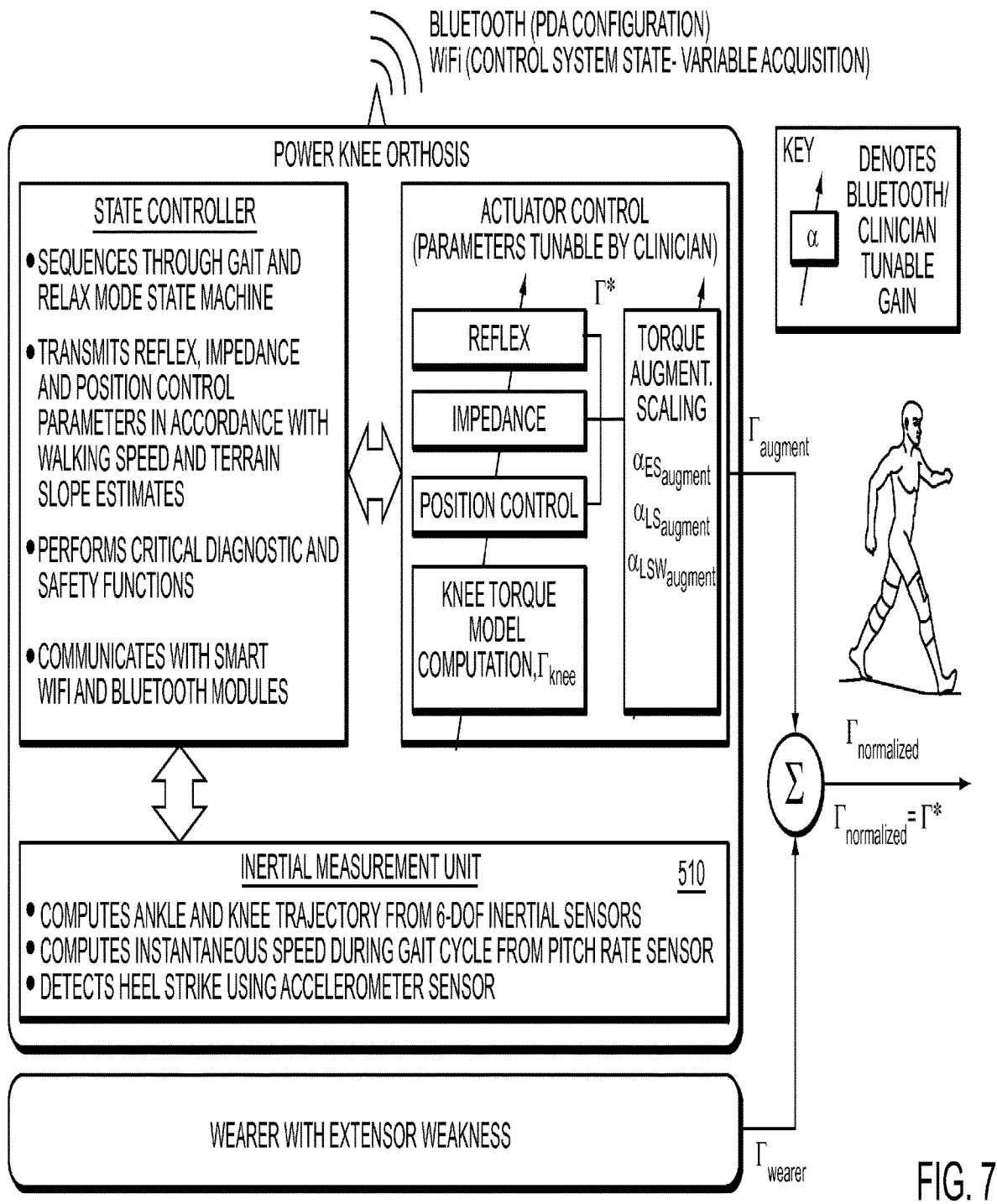
FIG. 7 illustrates the operation of a powered augmentation device implementing the state machine of FIG. 6, according to one embodiment.

FIG. 7 illustrates how the PKO platform 500 can augment the torque of a wearer to achieve at least a normalized biomimetic response. In some embodiments, a powered augmentation device can augment the torque and adjust impedance to achieve a response that can enable a wearer who does not have a diminished natural joint function to perform activities such as walking or running a long distance, carrying a heavy load, climbing steep slopes, etc. The state machine 600 modulates the SEA 502 impedance, reflex, and position control response in accordance with gait speed and terrain modality inputs from the IMU 510. The SEA 502 control internally computes at least the normalized biomimetic torque, $\Gamma^*$, in each state of the gait cycle. State-specific attenuation, set by the clinician, then scales $\Gamma^*$ and drives the SEA 502 to deliver just the right torque, $\Gamma_{augment}$, to add to the wearer's natural torque response, $\Gamma_{wearer}$, to approximate $\Gamma^*$, i.e., the desired normalized biomimetic response or an enhanced response that may allow a person to undertake activities such as walking fast (e.g., 2 m/sec.) for a long time e.g., about 6 hours.

Battery conservation is important in wearable PKO devices. In the absence of battery energy, or when the walking state machine (e.g., the state machine 600, illustrated with reference to FIG. 6) detects that the wearer has stopped walking (which can be determined by absence of gait-cycle phase transition for over approximately two seconds), the control system shorts the motor leads to ground using power electronics. In this special damping mode the motor leads are shorted together, creating a dynamic brake with damping torque, $\tau_{motor}=-b_{sl}\omega=-(k_g k_t)^2/R\omega$, where $b_{sl}$ is the shorted leads damping, $k_g$ is the gear ratio between the motor and joint output, $k_t$ is the motor constant in Nm/A and R is the motor resistance, and $\omega$ is the rotation rate of the joint. In the "shorted leads" operation, the time constant, $\tau_{sl}$, that describes the first-order spring-damper actuator dynamics comprising the series-spring, $k_{SEA}$ and the intrinsic actuator damping, $b_{sl}$, is given by the relation, $$\mathcal{T}_{sl} = \frac{b_{sl}}{k_{SEA}}.$$

In transverse-flux and other high-torque motor actuators, the $\tau_{sl}$ may be on the order of about 500 msec or more. For time intervals, e.g., less than ⅓ of the time constant, the actuator 502 in "shorted leads" mimics a static clutch, taking no energy from the battery. By matching the series-stiffness with that required in early stance flexion, the motor clutch is engaged at the desired joint equilibrium so as to approximate the biomimetic linear spring response without requiring any battery energy. This affords significant advantage in system design, response, and economy of operation.

Figure 8A:
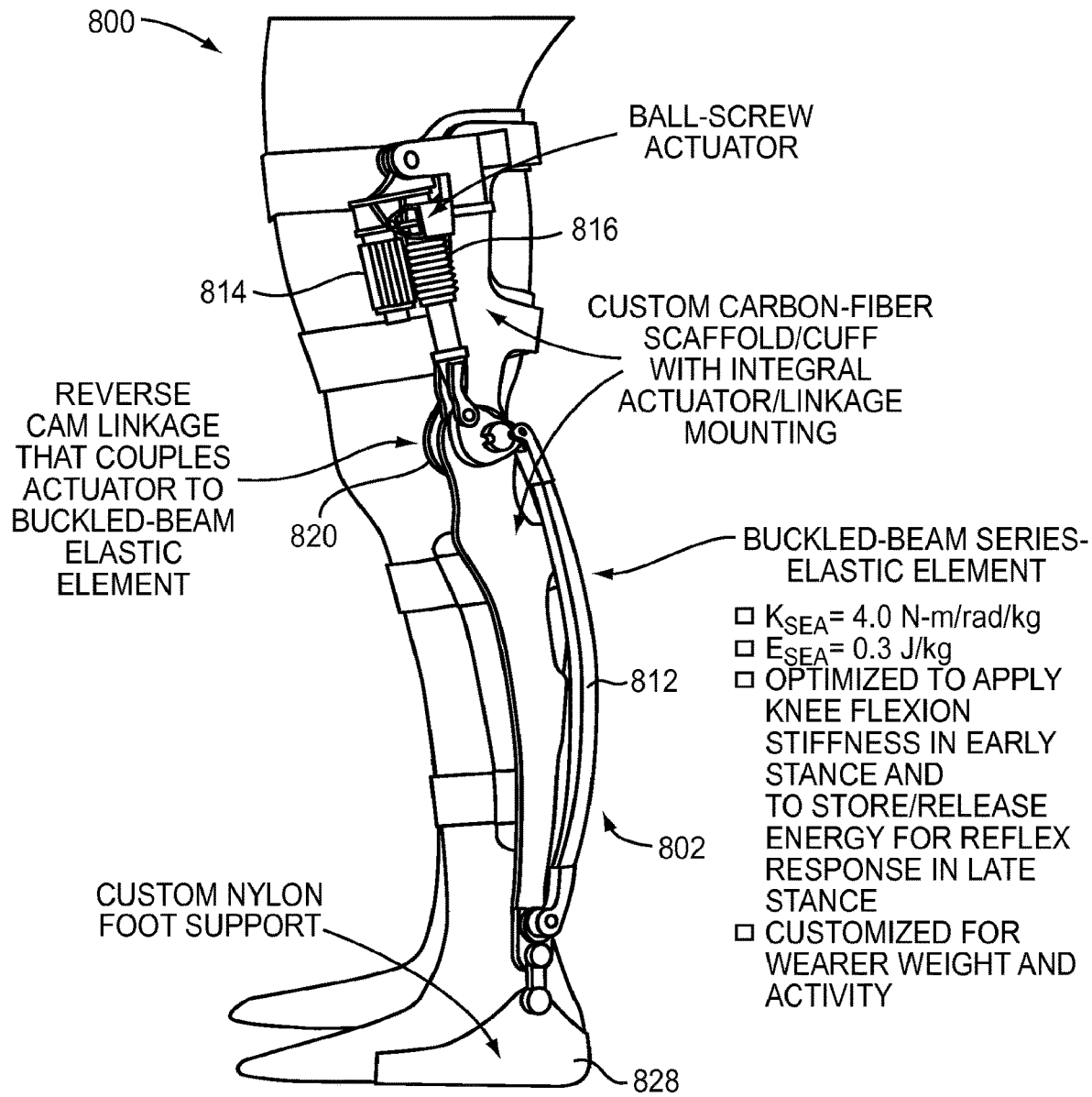
FIGS. 8a-8c schematically depict a powered augmentation device according to another embodiment.
Figure 8B:
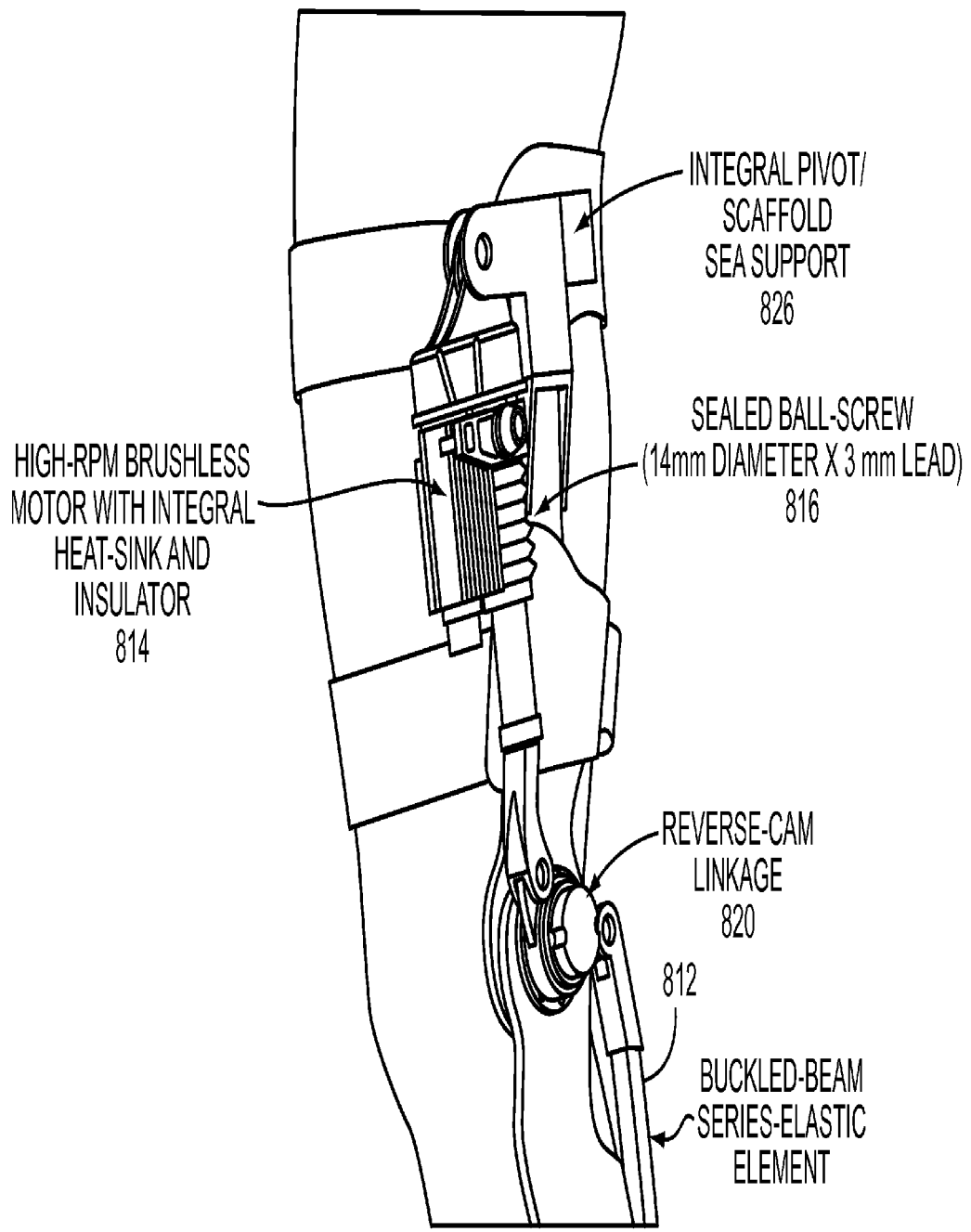
Figure 8C:
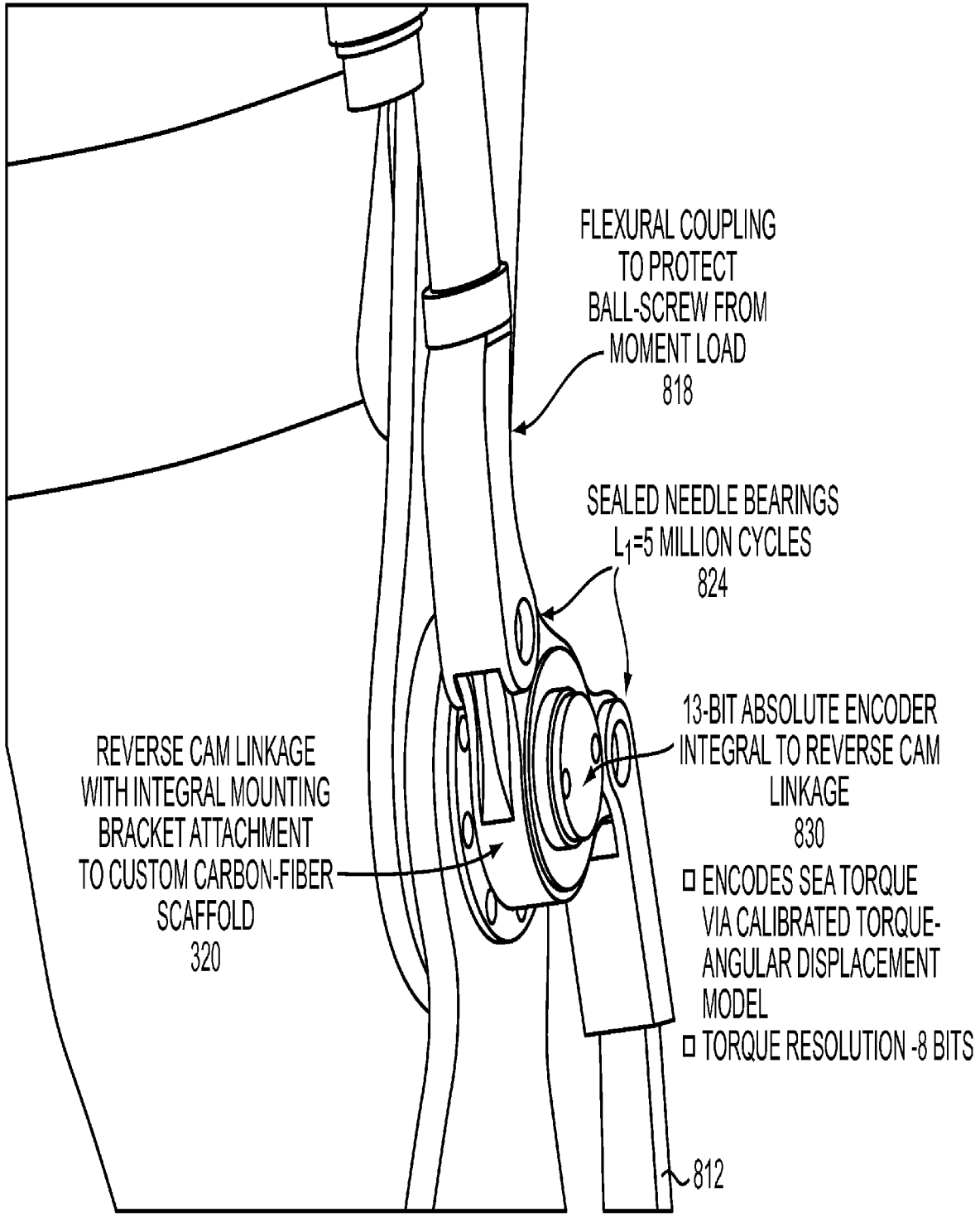

FIGS. 8a-8c depict a PKO device 800 that employs a buckled beam 812 as the series-elastic element of the SEA 802. The SEA 802 includes a high RPM brushless, permanent magnet motor 814 having an integral heat sink and an insulator. The motor 814 can be a radial motor, a transverse-flux motor, a stepping motor, etc. The SEA 802 also includes a sealed ball-screw mechanism 816 having a 14 mm diameter and 3 mm lead, in this embodiment. It should be understood that these dimensions are illustrative only and are not limiting.

The motor 814 is coupled to the buckled beam via a flexural coupling 818 to protect the ball-screw mechanism 816 from moment load, a reverse-cam linkage 820, and sealed needle bearings 824. The needle bearings 824 typically have L1 design life of over five million cycles (i.e., a design whereby 99% of a population survive longer than the reported design life with 95% statistical confidence). The PKO 800 also includes an integral pivot scaffold SEA support 826, coupled to the motor 814, and a foot support 828 (e.g., a custom nylon foot support), coupled to the buckled beam 812. The reverse-cam linkage 820 includes an encoder 830 that may be used to determine the SEA torque based on a torque-angular displacement model. The encoder 830 can be a 13-bit absolute encoder having a torque resolution of about 8 bits.

Figure 8D:
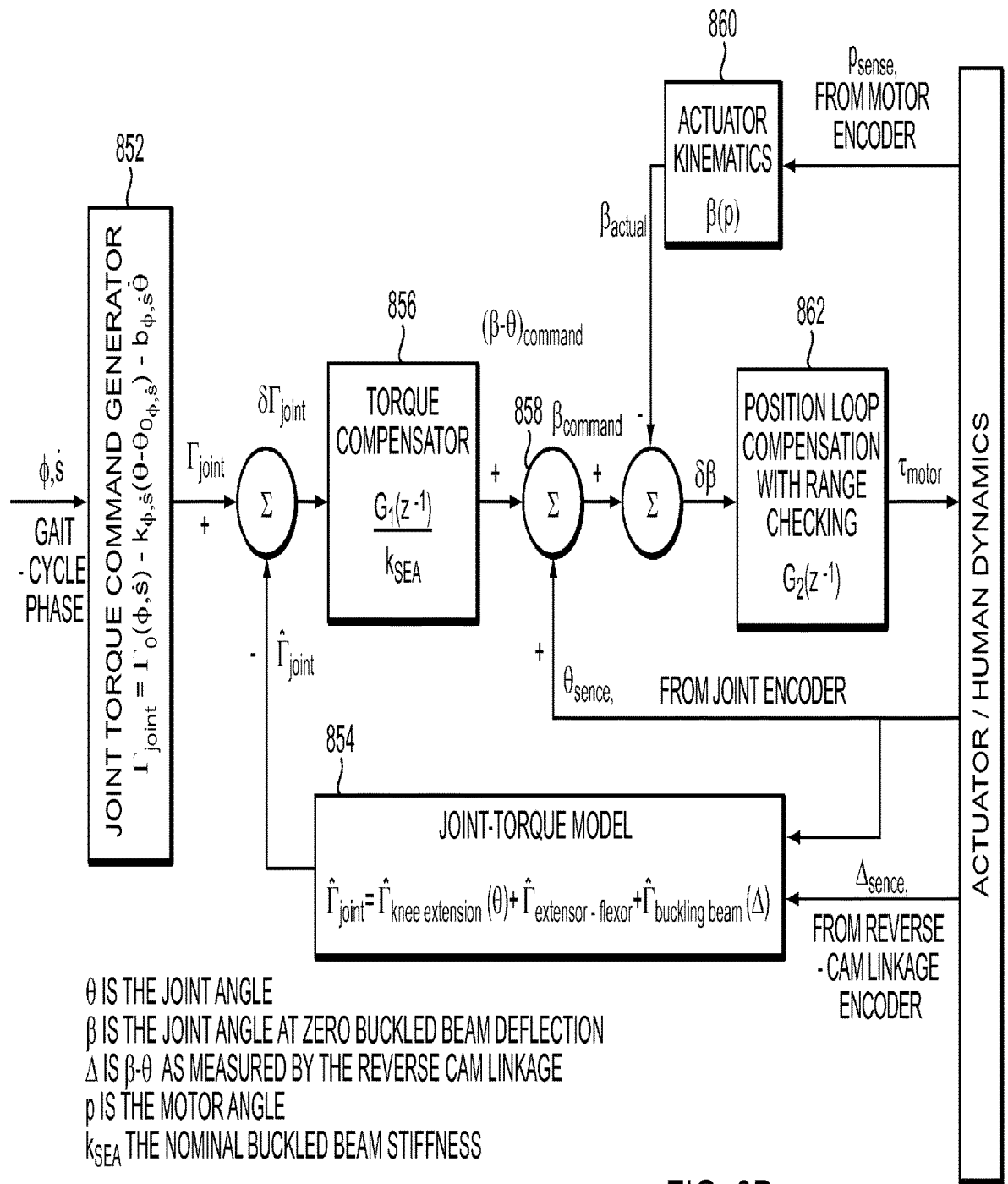
FIGS. 8d and 8e illustrate closed-loop control of the powered augmentation device depicted in FIGS. 8a-8c, according to two embodiments, respectively.

In one embodiment, the motor 814 is controlled in a closed loop. FIG. 8d illustrates one embodiment of an implementation of the closed-loop torque control in the PKO 800, in which the Joint Torque Command Generator 852 computes the commanded joint torque, $\Gamma_{joint}$, from terrain, $\phi$, walking speed, $\dot{s}$, and gait-cycle phase as these are supplied from a State Controller (e.g., State and Actuator Controller 508, described with reference to FIG. 5). The Joint-Torque Model 854 estimates the actual applied joint torque, $\Gamma_{joint}$, from wearer knee extension, wearer extensor-flexor and buckling-beam 812 (for series-elasticity) torque contributions. The wearer contributions may be assumed to be a percentage of a normative amount or a percentage of the command torque. The contribution of the buckling-beam 812 (series elastic component of the SEA 802, in general) may be estimated from off-wearer calibration during testing of the PKO device 800.

The difference in the commanded and applied torque, $\delta\Gamma_{joint}$, is scaled by the nominal stiffness of the buckling beam 812 (generally, the SEA) and is passed through a proportional-integral-derivative (PID) compensator 856, $G_1(z^{-1})$, to compute a commanded value of deflection, $\beta-\theta$, where $\theta$ is the joint angle and $\beta$ is the joint angle specified by the actuator for approximately zero buckled beam (SEA) deflection. $G_1$ is designed with at least integral compensation with saturation error limits to force substantially zero steady-state torque error and may typically include proportional and derivative terms. The sensed joint angle, $\theta_{sense}$, is added by an adder 858 to the deflection command to compute a commanded actuator angle, $\beta_{commanded}$.

The estimated actuator displacement is derived by actuator kinematics 860 by sensing the motor angle, p, which is used in a computational model, $\beta(p)$, of the actuator kinematics 860. The actuator error is supplied to a second PID compensator 862 with actuator range of motion limits to deliver a motor torque, $\tau_{motor}$, to drive the actuator 802. A brushless, permanent magnet motor, either radial, transverse flux, or stepping motor, is commutated electronically using a multiphase motor driver that delivers a torque-producing current component, $i_q$, to achieve the desired motor torque via the relation $\tau_{motor}=k_t i_q$, where $k_t$ is the motor torque constant in Nm/A. If a stepping motor is used, the motor can be stepped in a closed-loop fashion to align with the position command.

Figure 8E:
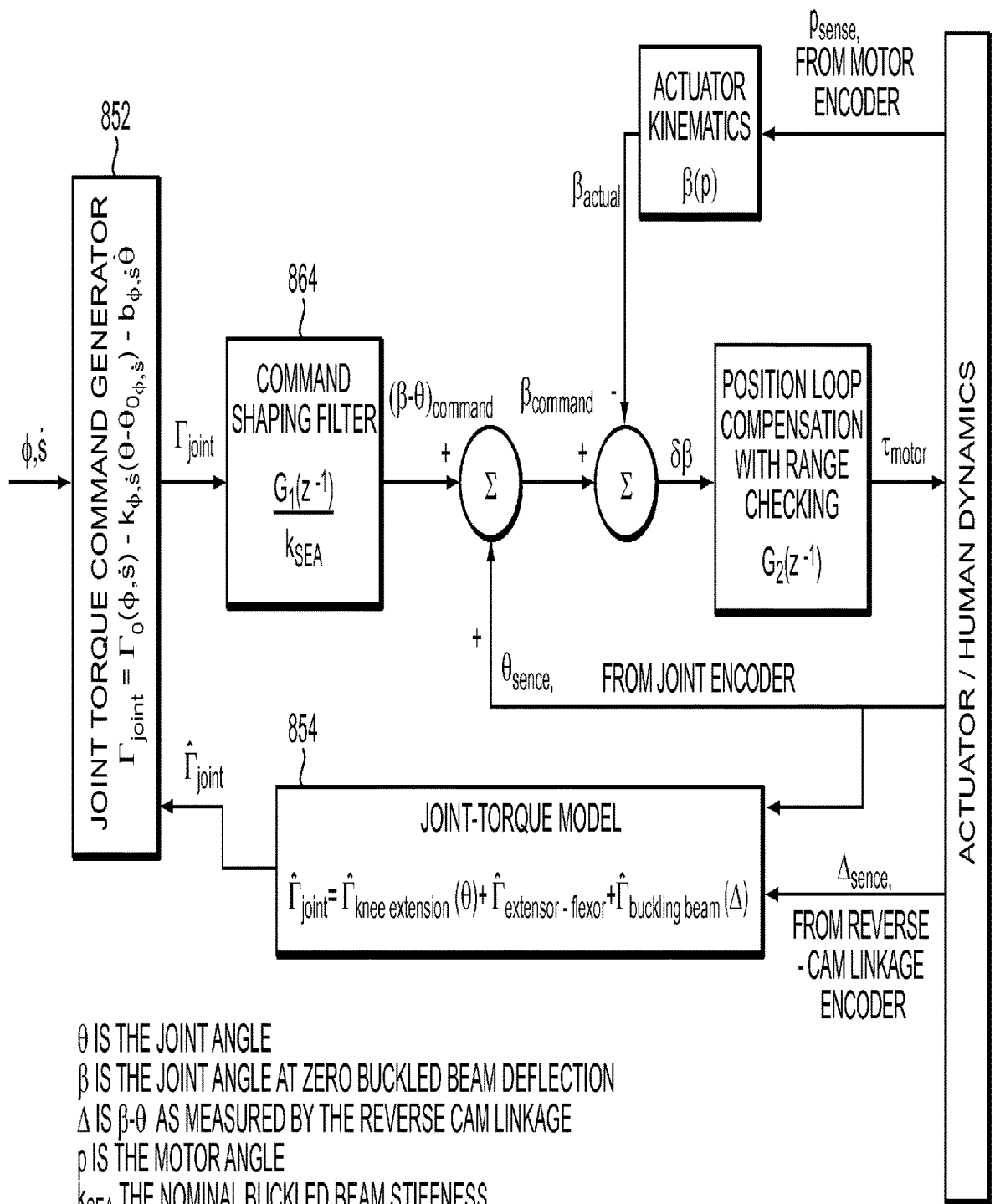

In another embodiment illustrated with reference to FIG. 8e, the Joint Torque Model 854 supplies and estimated joint torque to the Joint Torque Command generator 852, which determines the augmentation torque command, $\Gamma_{joint}$. The torque command is passed through a command shaping filter 864, having a transfer function $G_1 (z^{-1})$ and a torque de-scaling, $1/k_{SEA}$, to create a high-fidelity deflection signal. The command shaping filter 864 may be a low-pass filter to ensure that the inner deflection control loop has sufficient response bandwidth to follow the command. Other embodiments may be implemented by those skilled in the art to deliver a joint torque response that closely matches the desired biomechanical response as this is achieved through modulation of impedance, joint equilibrium, and torque in accordance with gait-cycle phase, terrain and walking speed.

Figure 9:
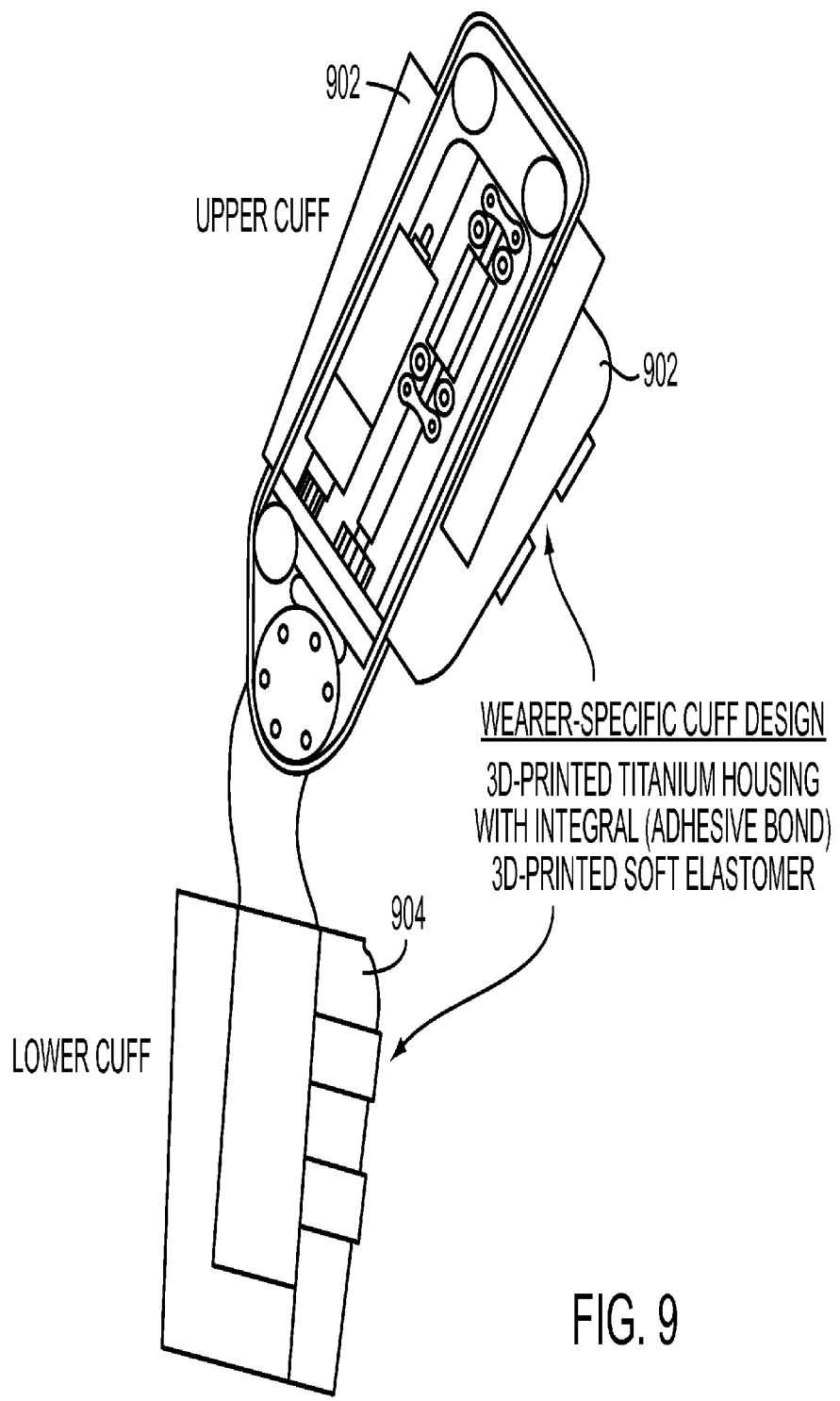
FIG. 9 illustrates seamless integration of a powered augmentation device with a leg of a human, according to one embodiment.

Seamless integration of the PKO platform 500 onto a wearer is desirable to ensure that the torque supplied by the PKO platform 500 is coupled efficiently to the joint (knee, ankle, etc.). With reference to FIG. 9, in some embodiments, a process is provided for custom manufacturing an upper cuff assembly 902 and a lower cuff assembly 904 to conform/couple directly to the wearer. For each wearer a three-dimensional scanning tool is employed to measure those body surfaces that must integrate with the PKO platform 500. From these surface measurements, lightweight titanium forms can be printed (e.g., using a direct-write process). These can be functionalized through heat treating to create the scaffold upon which a custom 3-D printed elastomer, with spatially-varying durometer, can be bonded to achieve the desired custom integration.

In some embodiments, the State and Actuator Controller 508 is adapted to kinematically reconstruct a joint path. Such reconstruction can be used to determine the terrain (e.g., whether the terrain is level ground, sloping ground, or stairs), and activity (i.e., whether the wearer is walking on level ground, upslope, or downslope, or walking up or down the stairs). The modulation of the toque, impedance, and joint equilibrium may be based on the terrain and activity as determined via the kinematic reconstruction.

Figure 10:
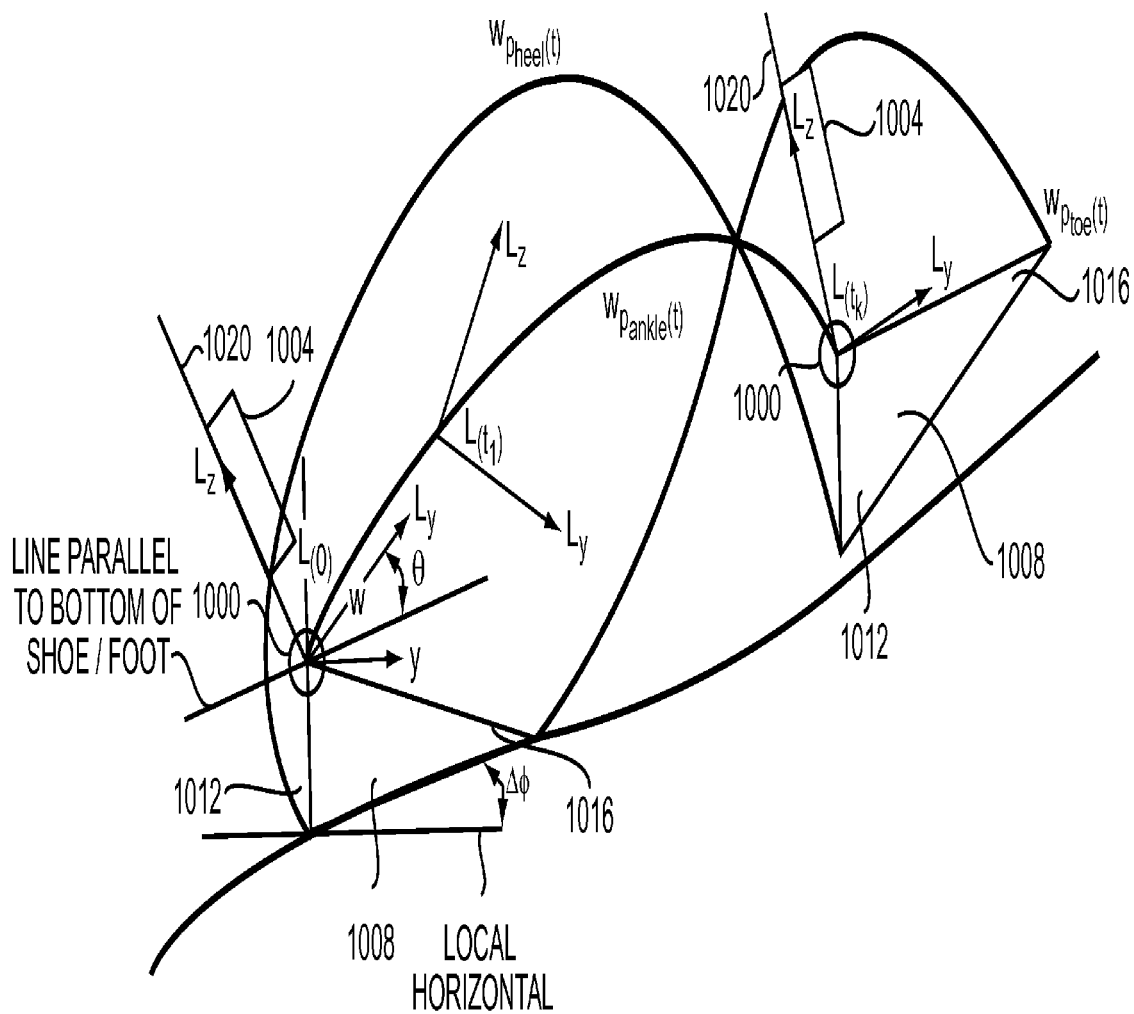
FIG. 10 depicts kinematic reconstruction by a controller for controlling a powered augmentation device according to one embodiment.

FIG. 10 illustrates a method for determining, via kinematic reconstruction, ankle joint 1000, heel 1012 and toe 1016 paths while using any PKO device (e.g., the PKO platforms 500, 800) based on the inertial pose of a lower leg member 1020 coupled to the ankle joint 1000, and the angle between the lower leg member 1020 and foot member 1008. Pose is the position and orientation of a coordinate system. The IMU (e.g., the IMU 510) may be coupled to the lower leg member 1020. The IMU may include a three-axis rate gyro for measuring angular rate and a three-axis accelerometer for measuring acceleration. Placing the inertial measurement unit on the lower leg member 1020 collocates the measurement of angular rate and acceleration for all three axes of the lower leg member 1020. The inertial measurement unit provides a six-degree-of-freedom estimate of the lower leg member 1020 pose, inertial (world frame referenced) orientation and ankle-joint 1000 (center of rotation of the ankle-foot) location.

In some embodiments, the lower leg member 1020 pose is used to compute the instantaneous location of the knee joint. By using knowledge of the ankle joint 1000 angle ($\theta$) the instantaneous pose of the bottom of the foot 1008 can be computed, including location of the heel 1012 and toe 1016. This information in turn can be used when the foot member 1008 is flat to measure the terrain angle in the plane defined by the rotational axis of the ankle joint/foot member. Mounting the inertial measurement unit on the lower leg member 1020 has advantages over other potential locations. Unlike if it were mounted on the foot member 1008, the lower leg member 1020 mounting protects against physical abuse and keeps it away from water exposure. Further, it eliminates the cable tether that would otherwise be needed if it were on the foot member 1008—thereby ensuring mechanical and electrical integrity. Finally, the lower leg member 1020 is centrally located within the kinematic chain of a hybrid system facilitating the computation of the thigh and torso pose with a minimum of additional sensors.

The inertial measurement unit can be used to calculate the orientation, $_{ankle}{}^{w}O$, position, $_{ankle}{}^{w}P$, and velocity, $_{ankle}{}^{w}v$, of the PKO platform in a ground-referenced world frame. $_{ankle}{}^{w}O$ may be represented by a quaternion or by a 3×3 matrix of unit vectors that define the orientation of the x, y and z axes of the ankle joint in relation to the world frame. The ankle joint 1000 coordinate frame is defined to be positioned at the center of the ankle joint axis of rotation with its orientation tied to the lower leg member 1020. From this central point, the position, velocity and acceleration can be computed. For points of interest in, for example, the foot (e.g., the heel 1012 or toe 1016), a foot member-to-ankle joint orientation transformation, $_{foot}{}^{ankle}O(\theta)$ is used to derive the position using the following relation:

$$_{point\text{-}of\text{-}interest}{}^{w}P = {}_{ankle}{}^{w}P + {}_{ankle}{}^{w}O(\gamma)_{foot}{}^{ankle}O(\theta)(^{foot}r_{point\text{-}of\text{-}interest})$$

where $$_{foot}^{ankle}O(\gamma) = \begin{bmatrix} 1 & 0 & 0 \\ 0 & \cos(\gamma) & -\sin(\gamma) \\ 0 & \sin(\gamma) & \cos(\gamma) \end{bmatrix}$$

where $\gamma$ is the inertial lower leg member angle, and $$_{foot}^{ankle}O(\theta) = \begin{bmatrix} 1 & 0 & 0 \\ 0 & \cos(\theta) & -\sin(\theta) \\ 0 & \sin(\theta) & \cos(\theta) \end{bmatrix}$$

where $\theta$ is the ankle joint angle.

In this embodiment, the inertial measurement unit, including the three-axis accelerometer and three-axis rate gyro, is located on the forward face at the top of the lower leg member 1020. It is advantageous to remove the effect of scale, drift and cross-coupling on the world-frame orientation, velocity and position estimates introduced by numerical integrations of the accelerometer and rate gyro signals Inertial navigation systems typically employ a zero-velocity update (ZVUP) periodically by averaging over an extended period of time, usually seconds to minutes. This placement of the inertial measurement unit is almost never stationary in the lower-extremity devices such as a PKO. However, the bottom of the foot is the only stationary location, and then only during the controlled dorsiflexion state of the gait cycle. An exemplary zero-velocity update method, which is not impacted by this limitation, for use with various embodiments of the invention is described further below.

To solve this problem, orientation, velocity and position integration of ankle joint is performed. After digitizing the inertial measurement unit acceleration, $^{IMU}a$, the ankle joint acceleration ($^{IMU}a_{ankle}$) is derived with the following rigid body dynamic equation:

$$^{IMU}a_{ankle} = {}^{IMU}a + {}^{IMU}\vec{\omega} \times {}^{IMU}\vec{\omega} \times X_{ankle}{}^{IMU}\vec{r} + \vec{\dot{\omega}} X_{ankle}{}^{IMU}\vec{r},$$

where $^{IMU}\vec{\omega}$ and $^{IMU}\vec{\dot{\omega}}$ are the vectors of angular rate and angular acceleration, respectively, in the inertial measurement unit frame and X denotes the cross-product.

The relationship is solved $_{ankle}{}^w O = {}_{IMU}{}^w O$ similarly as in the equations above using standard strapdown inertial measurement unit integration methods, in accordance with the following relationships known to one skilled in the art:

$$^w_{ankle}\dot{\Phi} = {}^w\Omega(^w\hat{\omega})^w_{ankle}\hat{\Phi}$$

$$^w\hat{v}_{ankle} = {}^w\hat{a}_{ankle} - [0, 0, g]^T$$

$$^w\hat{p}_{ankle} = {}^w\hat{v}_{ankle}$$

$$^w_{foot}\hat{\Phi} = {}^w_{ankle}\hat{\Phi}{}^{ankle}_{foot}\hat{\Phi} = {}^w_{ankle}\hat{\Phi} Rotation_x(\hat{\theta})$$

$$^w\hat{v}_{heel} = {}^w\hat{v}_{ankle} + {}^w\hat{\Omega}\big({}^w_{ankle}\hat{\Phi}\big[\hat{\dot{\theta}}\ 0\ 0\big]^T\big){}^w r_{heel-ankle}$$

$$^w\hat{v}_{toe} = {}^w\hat{v}_{ankle} + {}^w\hat{\Omega}\big({}^w_{ankle}\hat{\Phi}\big[\hat{\dot{\theta}}\ 0\ 0\big]^T\big){}^w r_{toe-ankle}$$

$$^w\hat{p}_{heel} = {}^w\hat{p}_{ankle} + {}^w r_{heel-ankle}$$

$$^w\hat{p}_{toe} = {}^w\hat{p}_{ankle} + {}^w r_{toe-ankle}$$

$$^w r_{heel-ankle} = {}^w_{foot}\hat{\Phi}^{foot}(r_{heel} - r_{ankle})$$

$$^w r_{toe-ankle} = {}^w_{foot}\hat{\Phi}^{foot}(r_{toe} - r_{ankle})$$

In the equations above, the matrix, $\hat{\Phi}$, will be used interchangeably with the orientation matrix, $_{IMU}{}^w O$. The world frame-referenced ankle joint velocity and position are then derived at a point in time after the time of the previous zero-velocity update (i-th zero-velocity update) based on the following:

$$^w v_{ankle}(t) = \int_{ZVUP(i)}^t ({}_{IMU}{}^w O)^{IMU} a_{ankle} dt$$

$$^w p_{ankle}(t) = \int_{ZVUP(i)}^t {}^w v_{ankle} dt$$

where $^w p_{ankle}(t=ZVUP(i))$ is reset to zero for all i.

Figure 11A:
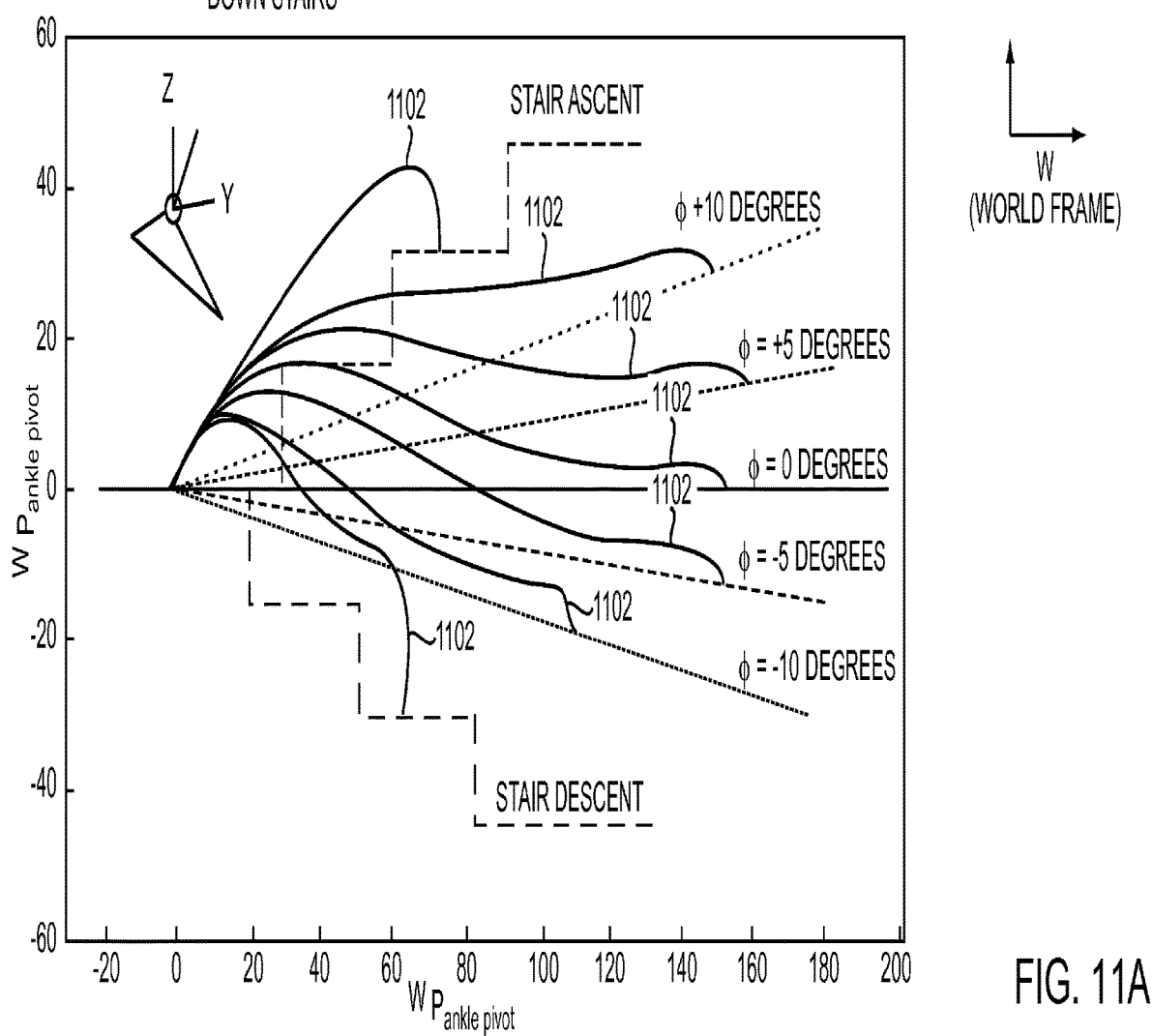
FIGS. 11a and 11b depict ankle and knee paths, respectively, each derived using measurements from an inertial measurement unit, according to one embodiment.

The six-degree-of-freedom inertial measurement unit (IMU) 510 of the PKO platform 500 or the IMU of the PKO device 800 is capable of computing the path of the ankle joint and the distal-end of the femur (knee) from which the IMU can discriminate and discern terrain modality—including stairs and slopes. With reference to FIG. 11a, inertially referenced ankle joint paths 1102, $^W p_{ankle\ joint}(t)$, and ankle-velocity-attack-angle 1104, $^W V_{ankle\ joint}$, on stairs and sloping ground can be used to discriminate stair ascent/descent from ascent/descent on sloping ground. The slope, $\phi$, can be estimated as $\hat{\phi}$ in swing using the relation:

$$\hat{\phi} = \tan^{-1}(^w p_{ankle\ joint_z}(t), {}^W p_{ankle\ joint_y})$$

Figure 11B:
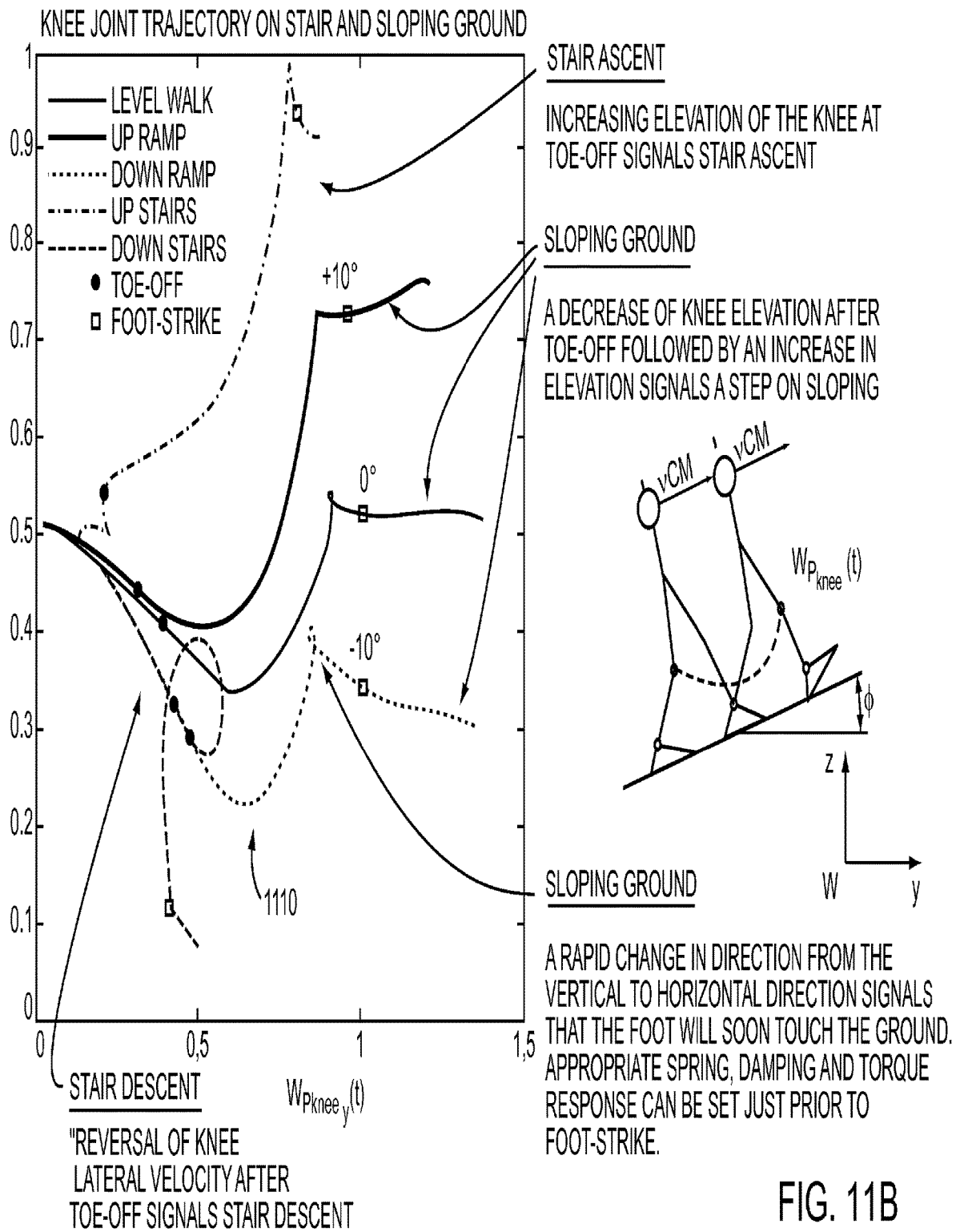

With reference to FIG. 11b, inertially-referenced knee path shape can be used to detect stair ascent/descent shortly after toe-off—enabling knee impedance and torque response to be configured prior to foot-strike on the stair. The "kink" 1110 in the knee path may signal impending foot strike on sloping ground, enabling a prediction of terrain slope using the ankle joint slope prediction described above with reference to FIG. 11a. Using the joint slope, speed and ankle velocity angle-of-attack, the joint equilibrium and impedance can be adjusted in preparation for the foot strike.

While the invention has been particularly shown and described with reference to specific embodiments, it will be understood by those skilled in the art that various changes in form and detail may be made therein without departing from the spirit and scope of the invention as defined by the appended claims. The scope of the invention is thus indicated by the appended claims and all changes that come within the meaning and range of equivalency of the claims are therefore intended to be embraced.

What is claimed is:

1. A method for assisting a person walking on a surface with a powered human augmentation device including a controller and a joint capable of exhibiting an impedance, the method comprising the steps of:
   determining a phase of a gait cycle;
   estimating within the gait cycle, that a slope of the surface is a negative slope;
   supplying to the joint a value for the impedance, the impedance comprising a linear spring component and a damping component; and
   modulating the impedance based on the phase of the gait cycle and the estimated slope to provide at least a biomimetic response, wherein the modulating comprises varying the damping component in accordance with an angle of the negative slope.

2. The method of claim 1, wherein the estimated slope is indicative of a walking mode such that level-ground walking mode corresponds to a substantially zero slope, downslope walking mode corresponds to a negative slope, and upslope walking mode corresponds to a positive slope.

3. The method of claim 2, wherein the downslope walking mode comprises descending stairs and the upslope walking mode comprises ascending stairs.

4. The method of claim 1, wherein the joint is a knee.

5. The method of claim 1 further comprising estimating walking speed, wherein at least one of the augmentation torque and the impedance is based on the estimated walking speed.

6. The method of claim 1, further comprising re-determining the phase of the gait cycle and re-estimating the slope wherein if the re-determined phase of the gait cycle is determined to be one of early stance and mid stance and the re-estimated slope is substantially zero, the impedance is modulated such that contribution of the linear spring component to the modulated impedance is greater than contribution of the damping component.

7. The method of claim 1, further comprising determining that the phase of the gait cycle is one of early stance and mid stance, wherein the impedance is modulated such that contribution of the damping component is increased substantially compared to a contribution thereof if the slope is estimated to be substantially zero.

8. The method of claim 1, further comprising re-determining the phase of the gait cycle and re-estimating the slope, wherein
   the augmentation torque comprises a non-conservative propulsive torque; and
   if the re-determined phase of the gait cycle is determined to be one of early stance and mid stance and the re-estimated slope is positive, providing the non-conservative propulsive torque such that the modulated augmentation torque is greater than the modulated augmentation torque applied if the slope is re-estimated to be substantially zero.

9. The method of claim 1, wherein if the phase of the gait cycle is determined to be late stance, the augmentation torque is modulated to correspond to a reflex torque that is related to the estimated slope.

10. The method of claim 1 further comprising the step of modeling, during a swing phase of the gait cycle, a joint equilibrium as a second-order response to a joint-position goal to be achieved prior to a next phase of the gait cycle.

11. The method of claim 10 further comprising the step of determining if the joint is substantially fully flexed, during a swing phase of the gait cycle, wherein modulating comprises adjusting both the augmentation torque and the impedance to be substantially zero, if the joint is determined to be substantially fully flexed.

12. The method of claim 10, wherein if the phase of the gait cycle is determined to be early swing, the augmentation torque is modulated according to the joint-equilibrium model such that a joint equilibrium corresponds to the joint-position goal.

13. The method of claim 10, wherein if the phase of the gait cycle is determined to be early swing, the impedance is modulated according to the joint-equilibrium model such that a joint equilibrium corresponds to the joint-position goal.

14. The method of claim 1, wherein estimating the slope comprises kinematically reconstructing a path of the joint within the gait cycle.

15. The method of claim 14 further comprising the steps of:
kinematically reconstructing a path of another joint within the gait cycle; and associating the path of the other joint with the path of the joint to estimate the slope.

16. The method of claim 14, wherein the kinematic reconstruction comprises computing a pose and an origin of a co-ordinate frame associated with a link connected to at least one of the joint and another joint proximal to the joint.

17. The method of claim 16, wherein computing the pose comprises creating a homogeneous transformation of the co-ordinate frame.

18. The method of claim 17, wherein the homogeneous transformation comprises: a 3×1 vector defining an origin of the co-ordinate frame; and
a 3×3 matrix comprising unit vectors of the co-ordinate frame.

19. The method of claim 16, wherein at least one point within the co-ordinate frame corresponds to a link connected to at least one of the joint and another joint proximal to the joint.

20. The method of claim 16, wherein at least one point in the coordinate frame corresponds to a link connected to an ankle joint proximal to the joint and the at least one point is at least one of a distal end and a proximal end of a tibia connected to the ankle.

21. The method of claim 1, wherein the augmentation torque is modulated according to a positive-force feedback.

22. The method of claim 21, wherein the augmentation torque modulated according to the positive-force feedback, in combination with a natural joint torque supplied by the human, approximates at least a normal joint torque.

23. The method of claim 21, wherein the positive-force feedback comprises a gain and an exponent.

24. The method of claim 23, wherein modulating comprises adjusting at least one of the gain and the exponent according to at least one of the estimated slope and walking speed.

25. The method of claim 1, wherein the augmentation torque is modulated according to a scaling factor.

26. The method of claim 1 further comprising the step of attenuating the augmentation torque to be applied according to a protocol.

27. The method of claim 1, wherein the augmentation torque is supplied in addition to natural joint torque supplied by the person to achieve at least a pre-determined total joint torque response.

28. The method of claim 1, wherein modulating comprises applying a closed-loop torque control at the joint.

29. The method of claim 28 further comprising:
modeling the joint torque; and
determining the phase of the gait cycle based on the joint torque model.

30. The method of claim 1, wherein the augmentation torque, the impedance, and a joint equilibrium are modulated in order to achieve at least a target walking speed.

31. The method of claim 1, wherein the augmentation torque, the impedance, and a joint equilibrium are modulated in order to substantially achieve a metabolic economy in accordance with a normative reference across at least one of walking speed and terrain.

* * * * *